(12) United States Patent
Willison et al.

(10) Patent No.: US 7,018,791 B1
(45) Date of Patent: Mar. 28, 2006

(54) BINDING COMPLEXES

(75) Inventors: Keith Willison, London (GB); Gillian Hynes, London (GB); Anthony Kian-Fong Liou, Singapore (SG)

(73) Assignees: Institute of Cancer Research: Royal Cancer Hospital, London (GB); Cancer Research Campaign Technology Limited, London (GB)

( * ) Notice: Subject to any disclaimer, the term of this patent is extended or adjusted under 35 U.S.C. 154(b) by 0 days.

(21) Appl. No.: 09/423,351

(22) PCT Filed: May 22, 1998

(86) PCT No.: PCT/GB98/01485

§ 371 (c)(1),
(2), (4) Date: Nov. 22, 1999

(87) PCT Pub. No.: WO98/53322

PCT Pub. Date: Nov. 26, 1998

(30) Foreign Application Priority Data

May 23, 1997 (GB) .................................... 9710762

(51) Int. Cl.
*G01N 33/50* (2006.01)
*G01N 33/53* (2006.01)

(52) U.S. Cl. .................... 435/4; 435/7.8; 435/7.92; 536/503

(58) Field of Classification Search .................. 435/4, 435/7.1, 7.3, 7.8, 7.9, 7.92; 436/501; 536/503
See application file for complete search history.

(56) References Cited

FOREIGN PATENT DOCUMENTS

| | | | |
|---|---|---|---|
| GB | 2 270 076 A | 3/1994 | |
| WO | WO 93/25681 | 12/1993 | |
| WO | WO 95/20654 | 8/1995 | |
| WO | WO 98/13496 | 4/1998 | |
| WO | WO 98/24909 | 6/1998 | |

OTHER PUBLICATIONS

Kim et al, Trends in Biochemical Sciences, 1994, vol. 19, pp. 543-548.*
Smith et al (Abstract from the 9th International Congress on Immunology, 1995, pp. 671, abstract # 3982).*
Kubota et al (Gene, 1995, vol. 154, pp. 231-236).*
Hynes et al (Electrophoresis, 1996, vol. 17, pp. 1720-1727).*
Anthony K.F. Liou & Keith R. Sillison, "Elucidation of the subunit orientation in CCT (chaperonin containing TCP1) from the subunit composition of CCT micro-complexes", The EMBO Journal, vol. 16 No. 14 pp. 4311-4316, 1997, Oxford University Press, XP002079764.
Judith Frydman and Jörg Höhfeld, "Chaperons get in touch: the Hip-Hop connection", TIBS Mar. 22, 1997, pp. 87-92, Elsevier-Science Ltd.

* cited by examiner

*Primary Examiner*—Karen A. Canella
(74) *Attorney, Agent, or Firm*—Dann, Dorfman, Herrell and Skillman; Kathleen D. Rigaut

(57) ABSTRACT

The present invention relates to binding members that are capable of binding to and effecting the function of proteins useful in facilitating folding of large polypeptides. The present invention particularly relates to the chaperone CCT. The invention provides materials and methods for effecting the biological activity of CCT within the cell so as to prevent the folding to CCT substrates such as actin, tubulin or cyclin. The inventors provide specific binding members capable of occupying a CCT substrate binding site thereby preventing the substrate from binding. Further, the present invention provides methods for screening for such binding members which effect the biological activity of CCT.

18 Claims, 15 Drawing Sheets

A

```
                             555
                              |
Rabbit CCTα    ...AVHSGAL | D | D |
Mouse CCTα    ...AVHSGAL | D | D |
Mutant        ...AVHSGAL | N | D |
```

B

— DOUBLE SHIFT
— SINGLE SHIFT
— NO SHIFT

Two Antibody Molecules          One Antibody Molecule
coupled onto CCT                coupled onto CCT

→

Endogenous                      Mutant
CCT                             CCT

Fig 10

Peptide Sequences

| Reference Peptide No. | Peptide No. In Figure 11 | Peptide Sequence |
|---|---|---|
| 1 | 6 | APRAVFPSIVGRPRH |
| 2 | 7 | FPSIVGRPRHQGVMV |
| 3 | 8 | GRPRHQGVMVGMGQK |
| 4 | 61 | GGTTMYPGIADRMQK |
| 5 | 77 | PRHQGVMVGMGQKDS |
|   |   |   |
| 6 | 26 | TFNTPAMYVAIQAVL |
| 7 | 35 | LPHAILRLDLAGRDL |
| 8 | 70 | LASLSTFQQMWISKQ |
|   |   |   |
| 9 | 12 | DEAQSKRGILTLKYP |
| 10 | 28 | IQAVLSLYASGRTTG |
| 11 | 39 | KILTERGYSFTTTAE |
| 12 | 40 | RGYSFTTTAEREIVR |
| 13 | 47 | ASSSSLEKSYELPDG |
| 14 | 65 | APSTMKIKIIAPPER |
| 15 | 67 | APPERKYSVWIGGSI |

| | |
|---|---|
| Lane 1 Peptide 8 at 13.3 μM | (Biotin-SGSGGRPRHQGVMVGMGQK) |
| Lane 2 Peptide 8 at 1.33 μM | (Biotin-SGSGGRPRHQGVMVGMGQK) |
| Lane 3 Peptide 8.1 at 13.3 μM | (Biotin-SGSGARPRHQGVMVGMGQK) |
| Lane 4 Peptide 8.2 at 13.3 μM | (Biotin-SGSGGAPRHQGVMVGMGQK) |
| Lane 5 Peptide 8.3 at 13.3 μM | (Biotin-SGSGGRARHQGVMVGMGQK) |
| Lane 6 Peptide 8.4 at 13.3 μM | (Biotin-SGSGGRPAHQGVMVGMGQK) |
| Lane 7 Peptide 8.5 at 13.3 μM | (Biotin-SGSGGRPRAQGVMVGMGQK) |
| Lane 8 Peptide 8.6 at 13.3 μM | (Biotin-SGSGAAAAAQGVMVGMGQK) |

*Fig. 11a*

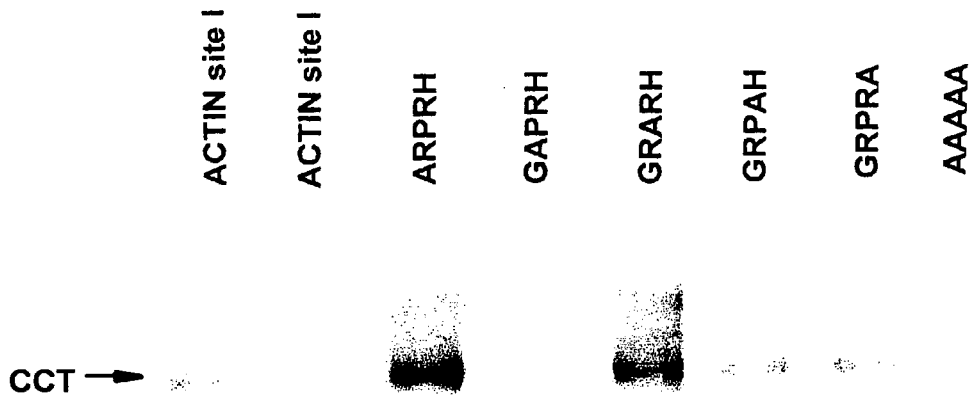

Fig 11b

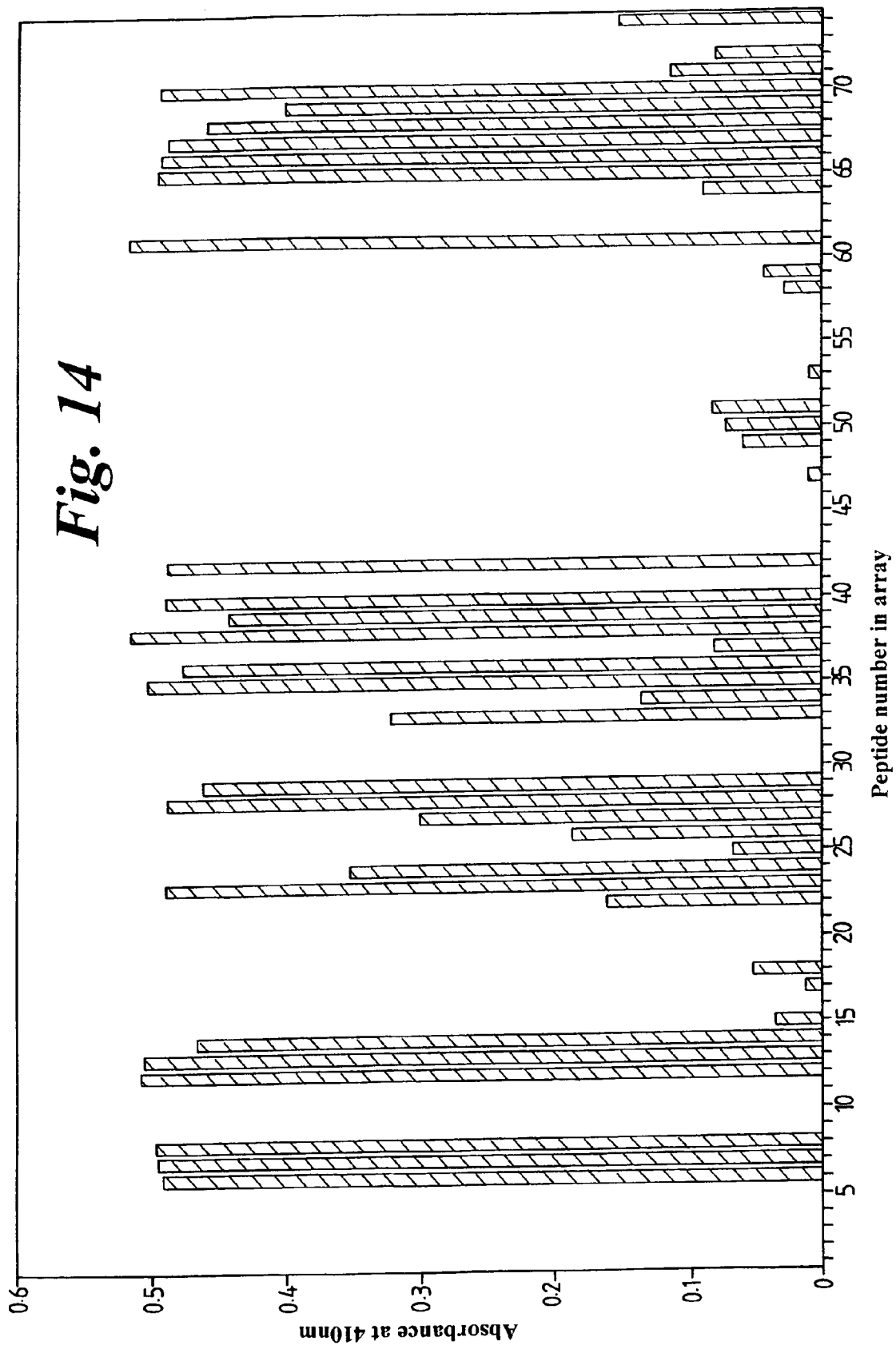

BINDING COMPLEXES

FIELD OF THE INVENTION

The present invention relates to binding complexes and binding members. Particularly, but not exclusively, the present invention relates to peptides and peptide fragments capable of binding to, and effecting the function of, proteins useful in facilitating folding of proteins. The present invention also relates to materials and methods for screening for such peptides or peptide fragments.

BACKGROUND OF THE INVENTION

Chaperones are a group of proteins that assist in the folding and refolding of other intracellular proteins. There are many kinds of molecular chaperones HSP100, HSP90, HSP70, Chaperonin (HSP60), DNAJ (HSP40), etc.

One particular family of Chaperones, the Chaperonins, is conserved in all organisms, eukaryotes, archaebacteria and eubacteria alike. The most well studied protein in this family is the eubacteria protein GroEL which has served as a model system for determining the mode of action of the chaperoning.

GroEL exists as a homopolymeric structure in the form of a double ring or toroid structure composed of 7 identical subunits per toroid. The double toroid binds to denatured or partially unfolded proteins and during repeated rounds of ATP hydrolysis achieves the correct folding of the bound protein. The ATPase active site of the individual subunits represents the most highly conserved region of the Chaperonin family of molecules and clearly this function is critical to the activity of Chaperonins from all species. When examining the primary sequence similarity across the Chaperonin family it is apparent that whilst the ATPase motif is highly conserved (Kim et al. Trends Biochem Sci., 1994; Kubota at el, Gene 154, 231–236, 1995a) outside this region there is only moderate or weak homology between the prokaryotic or endosymbiotically derived type I Chaperonins, GroEL, HSP60 and RBP and the type II Chaperonins of archaebacterium and eukaryotes namely TF55, Thermosomes and CCT (TCP1).

The generally accepted role for GroEL is that it binds to exposed hydrophobic regions of polypeptides that are normally buried within the cores of soluble proteins. By binding to the exposed hydrophobic regions the GroEL prevents aggregation between the unfolded protein monomers themselves or other intracellular molecules. Following substrate binding to GroEL, cycles of ATP hydrolysis drive the progression of the bound substrate towards a folded or near folded state which is then released from the folding complex. GroEL appears to be able to bind to many denatured proteins by means of interaction with hydrophobic pockets or clefts on the surface of the GroEL, indeed GroEL is able to bind to some 50% of denatured cytosolic proteins (Viitanen et al, Protein. Sci. 1, 363–369, 1992), which suggests a broad specificity for hydrophobic regions in substrate proteins. GroEL mediated folding and release of many substrates is facilitated by the ring co-chaperonin GroES which caps the active cis side of the folding complex (Weissman et al, Cell 84, 481–490, 1996).

By analysis the Type II Chaperonin from eukaryotes, CCT, appears to be an wholly different molecule to GroEL for a number of obvious structural and less obvious mechanistic reasons. CCT is a heteropolymeric complex comprised of eight different subunits in each of two rings which exist as a double toroid structure, the eight subunits being encoded by eight different genes. CCT also appears to bind a far more restricted spectrum of partially folded substrates than GroEL. CCT appears to primarily interact with proteins of the cytoskeleton, namely actin and tubulin, and indeed there are some denatured soluble proteins which CCT will simply not bind (Melki and Cowan, Mol. Cell Biol. 14, 2895–2904, 1994). CCT, like GroEL, possesses ATPase activity and the ATPase domain on each CCT subunit is the region showing highest homology with GroEL. There is no GroES like co-chaperonin known for any of the type II chaperonins.

The significantly greater complexity of CCT over and above that of GroEL might suggest that CCT possesses affinity for a wider spectrum of unfolded substrates than GroEL. This does not appear to be the case and therefore an alternate view on the reason for the greater complexity of CCT is that it performs a more complex role within eukaryotic cells than GroEL does in prokaryotic cells. Phylogenetic analysis points to an early divergence of prokaryotic and eukaryotic Chaperonins (Kubota et al, Curr.Biol., 4, 89–99, 1994) and if CCT evolved at a similar time to the emergence of the cytoskeleton then a specialist actin/tubulin binding function may well have evolved for this Chaperonin family member (Willison and Kubota,The Biology of Heat Shock Proteins and Molecular Chaperones, CSH Press, N.Y., U.S.A 1994).

The vast majority of analysis on Chaperonin substrates has been performed on GroEL, and consequently an appreciation of the breadth of substrates of CCT is more limited. Whilst several known substrates of CCT and CCT analogues have been reported, namely actin, tubulin neurofilament, firefly luciferase, chromaffin membrane components and hepatitis B virus capsid several other legitimate substrates of CCT remain to be identified (Hynes et al, Electrophoresis 17, 1720–1727, 1996). Recent studies have shown that a protein SRB is homologous to CCTδ and may be responsible for binding and enhancing the interaction of TRP-185 with TAR-RNA in HIV infected cells (Wu-Baer et al, J. Biol. Chem. 271, 4201–4208, 1996).

Very little data generated to date has pointed towards the structure, assembly or existence of intermediate sized CCT complexes. There have been two reports which suggest that perhaps CCT subunits act independently of the main 16 subunit double toroid structure.

In Xenopus (Dunn and Mercola, 1996) have shown that two subunits (a and y) are developmentally regulated and that high levels of expression in the neural crest tissues might represent the site of novel substrates for CCT.

Further evidence of the existence of micro-complexes comes from analysis of CCT in ND7/23 cells undergoing differentiation to a neuronal phenotype. Roobol et al have shown that CCTa enters neuritic processes and co-localises with actin at the leading edge of growth cone structures whereas three other CCT subunits remain predominantly in a perikaryl cytoplasmic region of the cell (Roobol et al 1995).

CCT is significantly more complex than GroEL in terms of subunit specificity, developmental expression and cellular localisation and recently further evidence of control of activity has come to light with the discovery of a novel post translational modification namely tyrosine adenylylation of CCT. Further evidence of post translational modification has been reported following isoelectric focusing analysis of CCT complexes where evidence of subunit isoforms was evident. If CCT does perform more complex cellular functions than just folding it is reasonable to assume that CCT subunits might be phosphorylated, adenylylated, myrisytolated etc., giving rise to apparent isoforms on 2D gel analysis, a phenomena manifest in proteins which are control points in cellular metabolism.

SUMMARY OF THE INVENTION

The present inventors have appreciated that CCT performs a different cellular role than GroEL manifest by a more complex subunit composition, isoforms, post-translational modification, differential cellular distribution and the existence of micro-complexes. The present inventors present here detailed and novel data that shows evidence of conserved micro-complex structure and a resulting solution to the proposed structure for the toroid. By determining the toroid structure, the present inventors further propose that distinct substrate binding regions on the complex may also exist which may be utilised in screening for interactions with both known and unknown cellular targets.

A previous filing by the present inventors (PCT/GB95/00192, WO95/20654) was concerned with cloning, sequence and use of the CCT subunits for the purposes of folding polypeptides. The embodiments presented herein pertain to the function of the complex in binding targets; conserved micro-complexes of CCT; structural determination of the CCT complex; the template directed dis-assembly of CCT; differential expression and cycling of CCT subunits; use of intact CCT, CCT micro-complexes or individual subunits or active portions thereof in the identification of binding members or mimetics thereof, or substrate binding partner binding epitope peptides (BEPs); use of binding members or BEPs, or their mimetics, in screening for drugs that interfere with cytoskeletal assembly; use of binding members or BEPs, or mimetics as therapeutics in their own right; production of antibodies to CCT or parts thereof, such as CCT micro-complexes, subunits or active portions thereof; use of anti-CCT/micro-complexes/subunit antibodies in screening and use of anti-CCT/micro-complexes/subunit antibodies as therapeutics in their own right.

At its most general, the present invention relates to materials and methods involved in the interaction of a CCT complex or part thereof and a binding member. The present inventors have realised that the interaction of binding members such as peptides and peptide fragments, with specific and distinct substrate binding sites on the CCT complex leads to an alteration in the biologically activity of the CCT complex within the cell structure.

Therefore, as a first aspect of the present invention, there is provided a binding member capable of occupying a CCT substrate binding site such that the normal biological activity of CCT within the cell is effected, said binding member being derived form a protein substrate of CCT. Preferably the substrate of CCT is actin, tubulin or cyclin and the binding member either comprises an amino acid sequence corresponding to a peptide fragment of the substrate or a mimetic thereof. More preferably, the amino acid sequence is up to 40 amino acids in length and even more preferaby 5 to 15 amino acids in length.

It is preferably that the binding member is capable of occupying a CCT substrate binding site so as to inhibit binding of the substrate at that site. In this way the substrate, e.g. actin, is prevented from being folded into its active form and, as a consequence, prevented from carrying out its normal biological functions within the cell.

In prefered embodiments of the present invention the binding member comprises an amino acid sequence having the at least 80%, preferably 85%, more preferably 90% and even more preferably 95% homology with any one of the amino acid sequences shown in FIG. 10.

As a further aspect, the present invention provides the use of a CCT complex or part thereof for identifying binding members capable of occupying a protein substrate binding site on said CCT complex or part thereof.

The CCT complex itself may be used to identify binding members, but preferably, micro-complexes, subunits or even fragments of the subunits, all containing a CCT substrate binding site are used. Alternatively, antibodies raised against a binding member as defined above may be used in a screening assay for further binding members.

As a further aspect of the present invention there is provided a method of identifying a binding member capable of occupying a substrate binding site on a CCT complex or part thereof, said method comprising contacting a candidate binding member with said CCT complex or part thereof and determining binding of said candidate binding member to said CCT complex or part thereof.

Therefore, binding members are agents which bind specifically to a CCT substrate binding site and are capable of effecting the biological activity of CCT within the cell. Binding members may be conveniently derived from substances known to bind CCT such as actin, tubulin or cyclin, for example. Preferably, the binding members are fragments of such substrates comprising a "binding epitope" of said substrate. These are referred to here as binding epitope peptides (BEPs). The present inventors describe herein specific BEPs and methods of screening for further BEPs or mimetics thereof.

For convenience, the following description of the invention relates to binding members being BEPs or mimetics thereof. However, the skilled person will appreciate that any agent, non-peptidyl or peptidyl may be used provided it binds specifically to a CCT substrate binding site such that it is capable of effecting the biologically activity of CCT in the cell, for example by inhibiting the interaction of the substrate and the CCT complex. Such binding members and mimetics thereof form further aspects of the present invention.

As mentioned above, the binding of the BEPs or mimetics thereof to the CCT substrate binding site preferably effects the normal biological activity of CCT within the cell. This may be achieved by either competitively preventing a protein to be folded, e.g. tubulin, from binding to the CCT complex such that the protein is prevented from becoming functional within the cell; or directly disrupting the function of the complex itself by effecting other distinct binding sites or by causing dis-assembly of the CCT complex itself so that it unable to preform as a Chaperone.

Once peptides or peptide fragments, which are capable of binding to substate binding sites on the CCT complex or part thereof have been determined, they may be modified, eg by mutagenesis so that their binding affinities may be improved. In the natural state, the CCT complex will bind subtrates and then release them again. It may be preferable to obtain a binding member that binds tightly to the CCT complex or part thereof so that it is not released in the normal way. Again modification of the peptides or peptide fragments may be carried out in order to achieve optimum binding characteristics.

Further, such peptides may be coupled with a coupling partner, preferable a second peptide derived from other than a substrate of CCT, to form of a fusion protein. Such second peptide may provide other characteristics such as the ability to cross a cell membrane so as to deliver the binding members into the cytoplasm.

The present invention further provides polypeptides comprising a CCT substrate binding site or active portion thereof. Preferably, said polypeptide will comprise an amino acid sequence having at least 80% homology with any one of the sequences for CCT apical domain residues even more preferably an amino acid sequence having at least 90% or 95% homology therewith.

Such CCT substrate binding sites or their active portions may be used in assays for screening for further binding members capable of modulating the interaction of a protein to be folded and the CCT complex. These binding members, as mentioned above, are preferably peptides and may be useful as peptide mimetics to inhibit the interaction of the CCT complex and the protein to be folded. Examples of such binding members include antibodies which may be raised against specific CCT substrate binding sites according to well known techniques. Such antibodies form a further aspect of the present invention and are described in more detail below.

Antibodies raised against binding members such as BEPs may form an alternative way of screening for further binding members from a peptide library. Again, such antibodies are included within the scope of the present invention and are described in more detail below.

As a further aspect of the invention, there is provided a pharmaceutical composition comprising binding members (BEPs) or mimetics thereof. Pharmaceutical compositions are described in more detail below.

Screening to Disrupt Binding of a CCT Substrate and the CCT Substrate Binding Site.

In a further aspect, the present invention provides assays using a CCT substrate, for example, actin, tubulin or cyclin, to find substances capable of modulating the interaction of the substrate with the CCT substrate binding site, these substances may also be useful as binding member mimetics to inhibit the interaction of a protein to be folded (substrate) and a CCT complex. Screening methods and assays are discussed in further detail below.

Variants and Derivatives

One class of binding members that can be used to disrupt the binding of proteins to be folded and a CCT substrate binding site are peptides based on the sequence motifs of proteins such as actin, tubulin or cyclin that interact with CCT. Such peptides tend to be small molecules, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6 5 or less in length. The present invention also encompasses peptides which are sequence variants or derivatives of a wild type binding protein (actin, tubulin or cyclin) sequence or fragment thereof, preferably comprising the binding epitope.

Preferably, the amino acid sequence shares homology with a fragment of the relevant peptide fragment sequence shown in FIG. 10 preferably at least about 30%, or 40%, or 50%, or 60%, or 70%, or 75%, or 80%, or 85% homology, or at least about 90% or 95% homology. Thus, a peptide fragment of actin, tubulin or cyclin may include 1, 2, 3, 4, 5, greater than 5, or greater than 10 amino acid alterations such as substitutions with respect to the wild-type sequence.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al, J. Mol. Biol., 215: 403–10, 1990, which is in standard use in the art. Homology may be over the full-length of the relevant peptide or over a contiguous sequence of about 5, 10, 15, 20, 25, 30 or 35 amino acids, compared with the relevant wild-type amino acid sequence.

As noted, variant peptide sequences and peptide and non-peptide analogues and mimetics may be employed, as discussed further below.

Various aspects of the present invention provide a substance, which may be a single molecule or a composition including two or more components, which includes a binding member which includes a sequence as recited above and/or disclosed elsewhere herein, a peptide consisting essentially of such a sequence, a peptide including a variant, derivative or analogue sequence, or a non-peptide analogue or mimetic which has the ability to occupy a CCT substrate binding site.

Variants include peptides in which individual amino acids can be substituted by other amino acids which are closely related as is understood in the art and indicated above. Non-peptide mimetics of peptides are discussed further below.

As noted, a peptide according to the present invention and for use in various aspects of the present invention may include or consist essentially of a fragment shown in FIG. 10. Where one or more additional amino acids are included, such amino acids may be from actin, tubulin or cyclin or may be heterologous or foreign to actin, tubulin or cyclin. A peptide may also be included within a larger fusion protein, particularly where the peptide is fused to a non-actin, tubulin or cyclin (i.e. heterologous or foreign) sequence, such as a polypeptide or protein domain.

Coupling Partners

The invention also includes derivatives of the peptides, including the peptide linked to a coupling partner, e.g. an effector molecule, a label, a drug, a toxin and/or a carrier or transport molecule. Techniques for coupling the peptides of the invention to both peptidyl and non-peptidyl coupling partners are well known in the art.

Synthesis

Peptides may be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Expression

Another convenient way of producing a peptidyl molecule according to the present invention (peptide or polypeptide) is to express nucleic acid encoding it, by use of nucleic acid in an expression system.

Accordingly the present invention also provides in various aspects nucleic acid encoding the polypeptides and peptides of the invention.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a polypeptide or peptide in accordance with the present invention can be readily prepared by the skilled person using the information and references contained herein and techniques known in the art (for example, see Sambrook, Fritsch and Maniatis, "Molecular Cloning, A Laboratory Manual, Cold Spring Harbor Laboratory Press, 1989, and Ausubel et al, Short Protocols in Molecular Biology, John Wiley and Sons, 1992), given the nucleic acid sequence and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding a CCT substrate may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the peptide binding members sequences can be made, e.g. using site directed mutagenesis, to lead to the expression of modified binding members peptide or to take account of codon preference in the host cells used to express the nucleic acid.

In order to obtain expression of the nucleic acid sequences, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of E. coli, yeast, and eukaryotic cells such as COS or CHO cells.

Thus, the present invention also encompasses a method of making a polypeptide or peptide (as disclosed), the method including expression from nucleic acid encoding the polypeptide or peptide (generally nucleic acid according to the invention). This may conveniently be achieved by growing a host cell in culture, containing such a vector, under appropriate conditions which cause or allow expression of the polypeptide. Polypeptides and peptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is E. coli.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing heterologous nucleic acid as disclosed herein.

Assays

In one general aspect, the present invention provides an assay for screening for binding members capable of occupying a substrate binding site on a CCT complex or part thereof comprising the steps of contacting a candidate binding member with said CCT complex or part thereof; and determining binding between said candidate binding member and the CCT complex or part thereof.

A candidate binding member found to bind to the relevant portion of a CCT substrate binding site may be tested for ability to disrupt CCT/substrate interaction and/or ability to affect CCT normal biological activity as discussed already above.

Performance of an assay method according to the present invention may be followed by isolation and/or manufacture and/or use of a compound, substance or molecule (all being binding members within the meaning of the present invention) which tests positive for ability to interfere with interaction between CCT and a CCT substrate described above and/or inhibit CCT activity.

The precise format of an assay of the invention may be varied by those of skill in the art using routine skill and knowledge. For example, interaction between binding members and CCT complex or parts thereof may be studied in vitro by labelling one with a detectable label and bringing it into contact with the other which has been immobilised on a solid support. Suitable detectable labels, especially for petidyl substances include $^{35}$S-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of an in vivo assay. The in vivo assay may be performed in a cell line such as a yeast strain or mammalian cell line in which the relevant polypeptides or peptides are expressed from one or more vectors introduced into the cell.

Antibodies

Antibodies directed to the site of interaction in either CCT substrate (binding epitopes) or CCT substrate binding sites form a further class of putative inhibitor compounds. Candidate inhibitor antibodies may be characterised and their binding regions determined to provide single chain antibodies and fragments thereof which are responsible for disrupting the interaction.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature 357: 80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

Following identification of a binding member which modulates or affects CCT biological activity, the binding member may be investigated further. Furthermore, it may be manufactured and/or used in preparation, i.e. manufacture or formulation, of a composition such as a medicament, pharmaceutical composition or drug. These may be administered to individuals.

As noted, the substance or agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the binding between the binding members disclosed herein and CCT complex. Examples of such analogues include chemical compounds which are modelled to resemble the three dimensional structure of the binding members.

In a further aspect, the present invention provides the use of the above substances in methods of designing or screening for mimetics of the substances.

Accordingly, the present invention provides a method of designing mimetics of binding members having the ability to occupy a CCT substrate binding site said method comprising:
(i) analysing said binding members to determine the amino acid residues essential and important for the ability of said binding member to occupy a CCT substrate binding site to define a pharmacophore; and,
(ii) modelling the pharmacophore to design and/or screen candidate mimetics having the the ability to occupy a CCT substrate binding site.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduced those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for further testing or optimisation, e.g. in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing. Mimetics of this type together with their use in therapy form a further aspect of the invention.

Pharmaceutical Uses

Generally, a binding member according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologicaly acceptable excipients. As noted below, a composition according to the present invention may include in addition to an inhibitor compound as disclosed, one or more other molecules of therapeutic use, such as an anti-tumour agent.

The present invention extends in various aspects not only to a binding member identified as a modulator of actin, tubulin or cyclin and CCT interaction in accordance with what is disclosed herein, but also a pharmaceutical composition, medicament, drug or other composition comprising such a binding member, a method comprising administration of such a composition to a patient, e.g. for anti-cancer, use of such a substance in manufacture of a composition for administration, e.g. for anti-cancer or similar treatment, and a method of making a pharmaceutical composition comprising admixing such a substance with a pharmaceutically acceptable excipient, vehicle or carrier, and optionally other ingredients.

The invention further provides a method of treating cancer which includes administering to a patient a binding member which interferes with the binding of actin, tubulin or cyclin to CCT.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, e.g. in a viral vector (a variant of the VDEPT technique—see below). The vector may targeted to the specific cells to be treated, or it may contain regulatory elements which are switched on more or less selectively by the target cells.

The binding member may be administered in a precursor form, for conversion to the active form by an activating agent produced in, or targeted to, the cells to be treated. This type of approach is sometimes known as ADEPT or VDEPT, the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially dependent upon the condition to be treated, such as cancer, virus infection or any other condition in which a CCT substrate such as actin, tubulin or cyclin, mediated effect is desirable.

Nucleic acid according to the present invention, encoding a polypeptide or peptide able to interfere with actin, tubulin or cyclin and CCT interaction or binding and/or induce or modulate CCT biological activity or other actin, tubulin or cyclin mediated cellular pathway or function, may be used in methods of gene therapy, for instance in treatment of individuals with the aim of preventing or curing (wholly or partially) a cancer.

A polypeptide, peptide or other substance able to interfere with the interaction of the CCT complex and its substrates as disclosed herein, or a nucleic acid molecule encoding a peptidyl such molecule, may be provided in a kit, e.g. sealed in a suitable container which protects its contents from the external environment. Such a kit may include instructions for use.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 10 shows the peptide sequences refered to in FIG. 11. The Reference Peptide Nos are the SEQ ID NOs of the listed peptide sequences.

FIG. 11 shows the interaction of actin derived peptides and alanine scanning mutations of actin derived peptides with CCT. Mouse testis CCT was incubated singly or in combination with peptide 8 (lanes 1 and 2; SEQ ID NO: 18), peptide 8.1 (lane 3; SEQ ID NO: 19), peptide 8.2 (lane 4, SEQ ID NO: 20), peptide 8.3 (lane 5; SEQ ID NO: 21), peptide 8.4 (lane 6; SEQ ID NO: 22), peptide 8.5 (lane 7; SEQ ID NO: 23), or peptide 8.6 (lane 8; SEQ ID NO: 24) as listed in FIG. 11A and 11C. In all lanes, CCT was incubated with peptide on ice for one hour. Samples were electrophoresed on 6% native gels, transferred to nitrocellulose membrane and incubated with Neutravidin-HRP (Pierce) at 2 μg per ml to reveal the distribution of biotinylated peptides. The arrowed region (FIG. 11B) shows CCT complexes bound by peptides. The sequences in FIG. 11B (lane 3, residues 5 to 9 of SEQ ID NO: 19; lane 4, residues 5 to 9 of SEQ ID NO: 20; lane 5, residues 5 to 9 of SEQ ID NO: 21; lane 6, residues 5 to 9 of SEQ ID NO: 22; lane 7, residues 5 to 9 of SEQ ID NO: 23; lane 8, SEQ ID NO: 122) are the core sequences of the mutant Actin Site I sequences present in the peptides listed in FIGS. 11A and 11C.

FIG. 14 shows in graphical form the absorbance at 410 nm for the peptides as illustrated in Table 2 to show that Groel recognises the same actin peptide sequences as CCT but also recognises several others in addition.

DETAILED DESCRIPTION

Definitions

Figure 1:
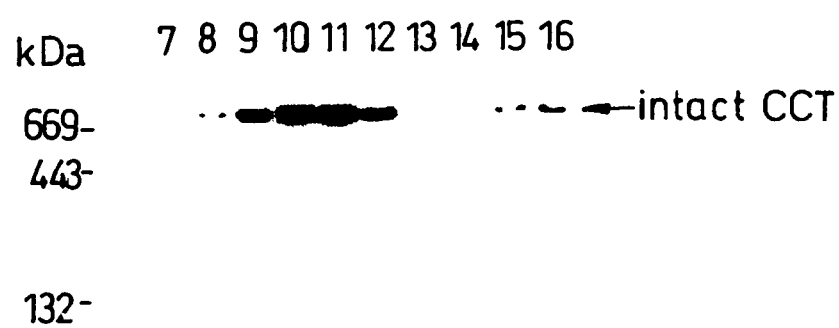
FIG. 1 shows multiple smaller complexes containing CCTa in sucrose fractions 13–16 (corresponding to sucrose densities 1.054 g/cm$^3$-1.030 g/cm$^3$). Mouse testis sucrose gradient fractions 7–16 (corresponding to sucrose densities 1.132 g/cm$^3$-1.030 g/cm$^3$) were resolved in a 6% non-denaturing polyacrylamide gel followed by Western blotting. The blot was then proved with monoclonal antibody 91A which recognises mouse CCTα. The distribution pattern of CCTα is revealed by chemiluminescence and two different exposure times are shown: A) 10 seconds; B) 2 minutes. The presence of smaller complexes containing CCTA is clearly shown in the longer exposure (B).
Figure 1:

"CCT" shall mean the complex comprising CCT subunits α, β, γ, δ, ε, ζ, η and θ in the form of a single or double toroid structure described in Kubota et al, Eur J. Biochem (1995) 230, p3–16.

Parts of the CCT complex are described below as a CCT micro-complex, a CCT subunit, or an active portion of a CCT subunit.

"CCT micro-complex" shall mean any combination of two or more CCT subunits.

"CCT subunit" shall mean any individual protein encoded by one of the CCT genes Ccta (CCT1), Cctb (CCT2), Cctc (CCT3), Cctd (CCT4), Ccte (CCT5), CctZ1, CctZ2 (CCT6), Ccth (CCT7) or Cctq (CCT8) described in Kubota et al, Eur. J. Biochem. (1995) 230, p3–16; Kubota et al, Gene (1995) 154 231–236; Kubota et al FEBS LETTERS (1997) 402 53–56.

"conserved CCT microcomplex" shall mean a combination of two or more CCT subunits which are adjacent in the double toroid structure defined in Liou and Willison (EMBO.J. 16, 4311–4316, 1997).

"CCT substrate" shall mean any protein which binds to CCT, CCT micro-complex or CCT subunit during the process of folding into native or semi native state or which binds to the aforesaid at times other than folding into native or semi native state.

"Binding epitope" shall mean the region on the substrate protein or binding partner that interacts with CCT, CCT micro-complex or CCT subunit.

"Substrate peptides" shall mean peptides defining the entire sequence of a substrate protein or binding partner used in the methods to define the binding epitope region.

"Binding epitope peptides (BEPs)" shall mean peptides which define the binding epitope region on the substrate or binding partner.

"an active portion" means a peptide which is less than the fragment of the substrate binding site or binding member amino acid sequence, but which retains the relevant property mentioned above.

"functional mimetic" means a substance which may not contain an active portion of the binding member amino acid sequence and is probably not a peptide at all, but which has the relevant property mentioned above.

"a derivative" means a peptide modified by varying its amino acid sequence, e.g. by manipulation of the nucleic acid encoding the peptide or by altering the peptide itself. Such derivatives of the natural amino acid sequence may involve insertion, addition, deletion or substitution of one or more amino acids, without fundamentally altering the essential activity of the peptides.

Suitable fragments of binding members or CCT substrate binding sites include those which include residues as identified herein. Smaller fragments, and derivatives, analogues and functional mimetics of this fragment may similarly be employed, e.g. peptides identified using a technique such as alanine scanning.

Identification of CCT Conserved Micro-Complexes

The enrichment of intact CCT from mouse testis post-nuclear supernatant (PNS) by a 10.2–40% continuous sucrose gradient has shown that this protein complex consistently sediments in fractions corresponding to 19–23% sucrose (Lewis et al, Nature 358, 249–252, 1992). The localisation of CCT in the sucrose gradient can be determined through probing, with the monoclonal antibody 91A that recognises mouse CCTα, and a Western blot of the gradient fractions. However, on prolonged exposure of the blot, via enhanced chemiluminescence, the distribution of CCTα extends to fractions corresponding to 10.2–18% sucrose (data not shown). These light sucrose fractions, when resolved by non-denaturing polyacrylamide gel electrophoresis followed by probing with monoclonal antibody 91A, showed several bands in addition to that representing intact CCT (FIGS. 1A and B). This distribution pattern of CCTα suggests the possible existence of smaller complexes comprising CCT subunits in these sucrose fractions. From here on, these smaller complexes are termed CCT micro-complexes to distinguish them from intact CCT.

Figure 2:
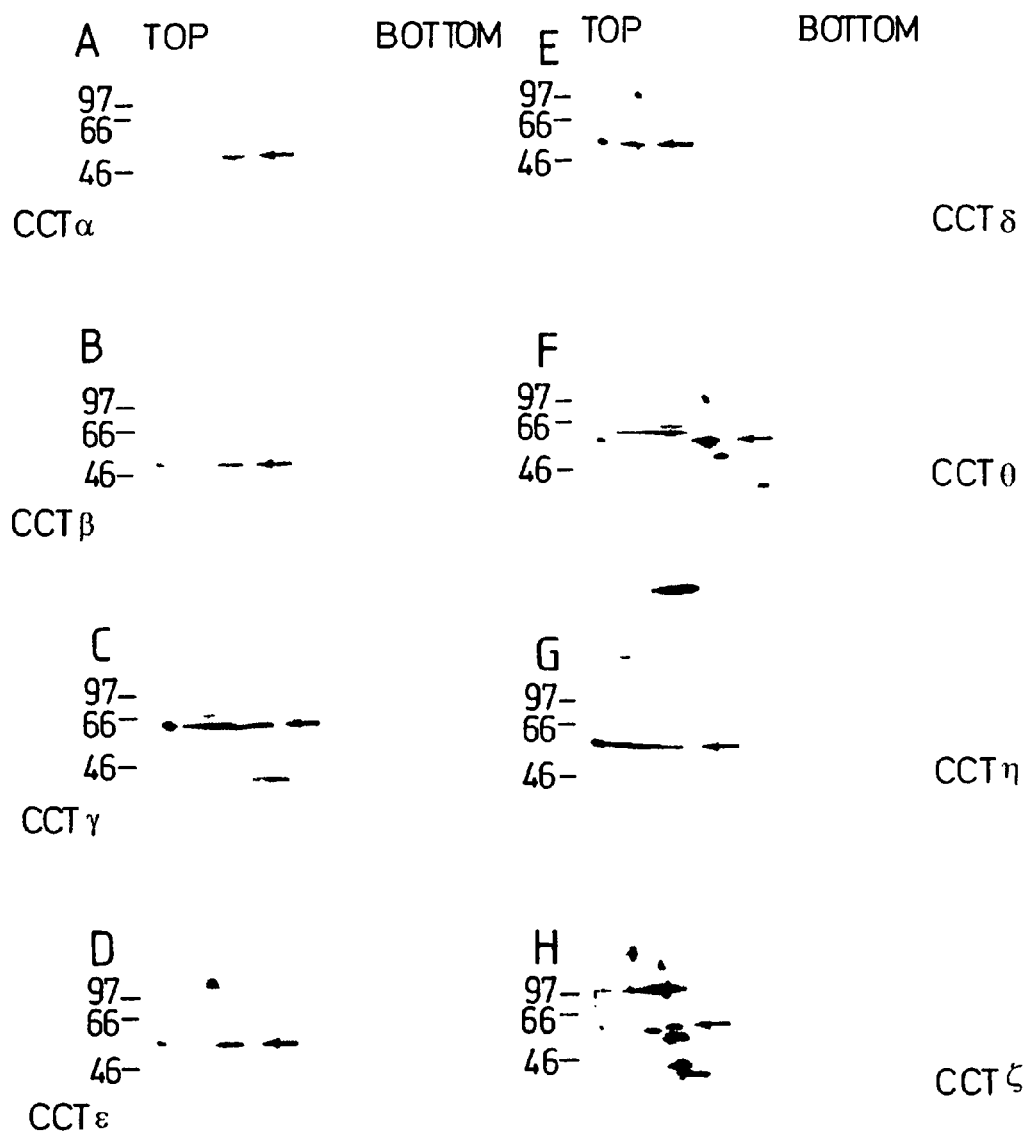
FIG. 2 shows the presence of CCT micro-complexes in sucrose gradient fraction 14 (corresponds to sucrose density 1.039 g/cm$^3$) form analysis by Semi Native Diagonal Electrophoresis (SNaDE) and Western blotting. Semi Native Diagonal Electrophoresis (SnaDE) analysis of the mouse testis sucrose fraction 14 shows the presence of intact CCT (lest most spot on the blot) and CCT micro-complexes (indicated by inner arrows). The "Top" and "Bottom" in the figure represent the orientation of the 6% non-denaturing gel slice that was further resolved in an 8% SDS PAGE gel. A Western blot of the SDS PAGE gel was probed sequentially with specific antibodies indicating the distribution patterns of A)CCTα; B)CCTβ; C)CCTγ; D)CCTε. Another identical Western blot was probed sequentially with the other four specific antibodies indicating the distribution patterns of E)CCTδ; F)CCTθ; G)CCTη and H) CCTζ.

Using the alternative technique of Semi-Native Diagonal Electrophoresis (SNaDE; non-denaturing gel electrophoresis in the first dimension followed by SDS-PAGE in the second dimension) and Western blotting, the presence of CCT micro-complexes in sucrose fraction 14 corresponding to sucrose density 1.039 g/cm$^3$ was examined in detail. FIG. 2 shows a single Western blot probed sequentially with eight specific antibodies, recognising different CCT subunits (CCTα, CCTβ, CCTγ, CCTδ, CCTε, CCTζ, CCTη and CCTθ), and with each antibody two signals are observed on the blot consistently. The signal on the left represents intact CCT since a similar and co-incident signal is obtained with all eight specific antibody probings. On the other hand, the signals on the right are generated from CCT subunits present as components of smaller complexes. The non-super-imposability of these signals when probed with different specific antibodies suggest the co-existence of many species of smaller complexes, each comprising a subset of the eight constitutively expressed CCT subunits, CCTα-CCTθ. The abundance of these various CCT micro-complexes is much less than intact CCT, probably less than 5% in total.

In FIG. 2, the complex patterns exhibited on the Western blots, (particularly those in panels F and H) were the result of non-specific cross-reactivity of the polyclonal antibodies against CCTθ and CCTξ used in the analysis. Nevertheless, the signals representing bona fide CCT subunits can be located by comparing their mobilities to the left-most signal representing the corresponding CCT subunit that migrates as a component of intact CCT. In this manner, the signals on the blots representing non-CCT subunits were identified and were excluded during subsequent analysis.

Size Distribution of CCT Micro-Complexes

Figure 3:
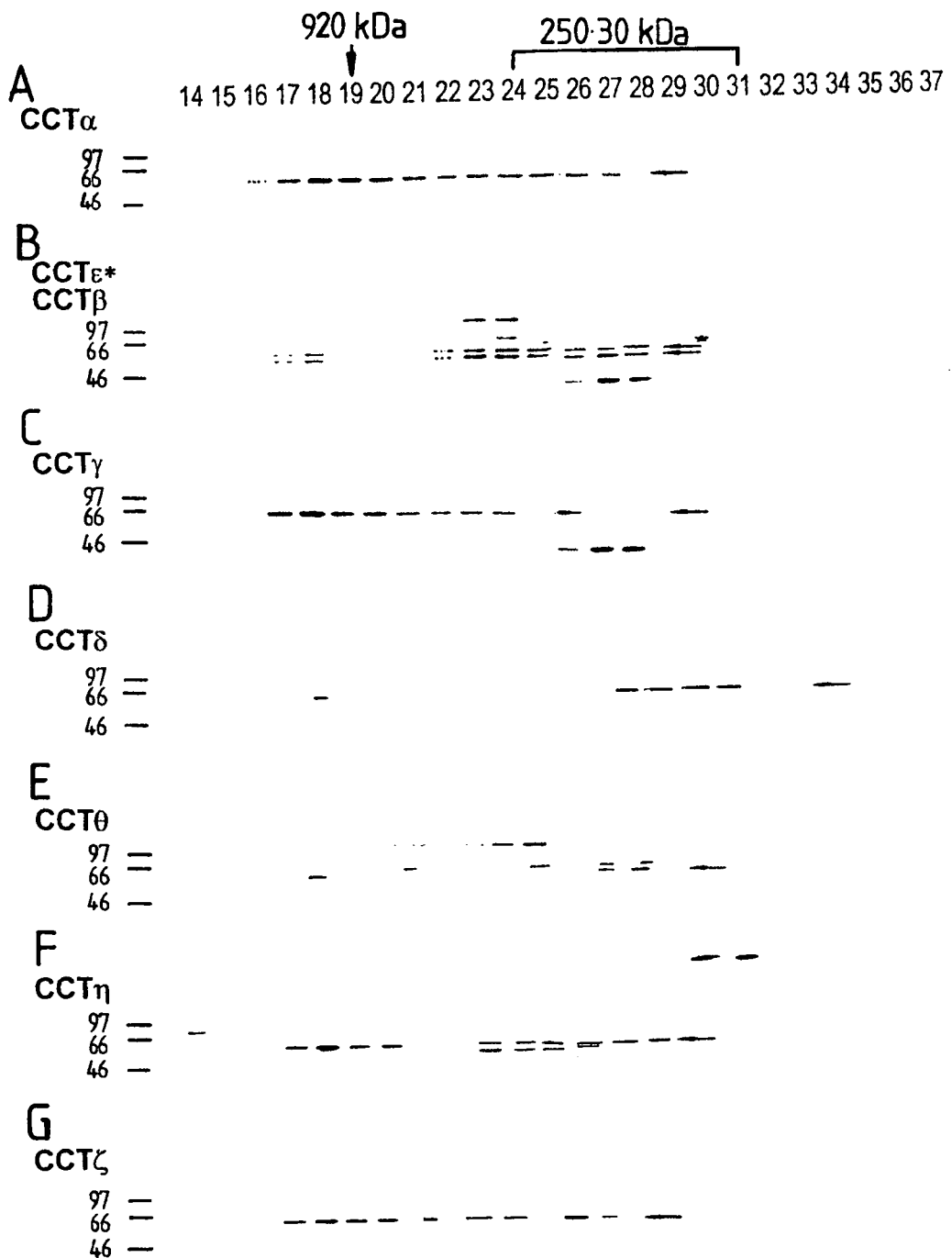
FIG. 3 shows the molecular size distribution of each CCT subunit type when present as components of CCT micro-complexes. CCT micro-complexes present in sucrose fraction 14–16 (corresponding to sucrose densities 1.039 g/cm$^3$-1.030 g/cm$^3$) were separated by gel filtration chromatography and the chromatographic fractions 14–37 (corresponding to molecular weight range of 2700–5 kDa) were resolved in an 8% SDS polyacrylamide gel followed by Western blotting. The blot was proved sequentially with specific antibodies recognising different CCT subunit to indicate their distribution patterns. Panels A–G showed the molecular size distributions of CCT micro-complexes containing A)CCTα; B)CCTβ; C)CCTγ; D)CCTε E)CCTδ; F)CCTθ; G)CCTη and H)CCTζ respectively. The band observed in fraction 19 which cross-reacted with all the specific antibodies used to identify CCT subunits and which has an estimated molecular weight of 920 kDa is intact CCT.

In order to determine the size distribution of the CCT micro-complexes and ensure that all of them are included in this analysis, sucrose fractions 14–16 (which correspond to sucrose densities of 1.068 g/cm$^3$–1.030/cm$^3$) were pooled and concentrated before being subjected to gel filtration chromatography using a Superose 6 column. Within the 40 resultant fractions obtained, all the CCT subunits were located within the molecular weight range of 5–2700 kDa (FIG. 3). Similar to the results obtained from the SNaDE analysis, all the CCT subunits were broadly located in two regions. In the first region, centering around fraction 19, a protein complex that has a molecular weight of approximately 920 kDa and is reactive with all the eight specific antibodies, is clearly intact CCT. On the other hand, the distinct cluster of bands in the second region, we attribute to CCT micro-complexes. During each probing with different specific antibodies, the distribution of these bands reflects the size distribution of the subset of CCT micro-complexes containing the respective CCT subunit type. Each CCT subunit type shows a different distribution pattern (FIG. 3) demonstrating a distinct size distribution for the micro-complexes containing each of these subunit types.

From the size distribution of each type of CCT subunit, it is probable that they exist not only as free subunits, but also as components of many larger complexes. To convey this point, we have classified CCT micro-complexes into three categories, (ie. 60–100 kDa, 100–150 kDa, 150–250 kDa) and we infer that they represent monomeric, dimeric and trimeric molecular states. The multiplicity of the molecular states for the subset of CCT micro-complexes containing each CCT subunits is obvious. For example, it seems that CCTθ exists only as monomer (i.e. 60 kDa) whereas CCTγ and CCTε are found to be present solely as components of larger complexes (i.e. >120 kDa). The remaining CCT subunits seem to exist as monomers and as components of larger complexes. It is probable that a subset of these complexes may comprise more than one type of CCT subunit.

Again, due to the non-specific cross reactivity for some of the polyclonal antibodies used, it is essential to identify the signals representing CCT subunits in order to ensure the accuracy of subsequent analysis. This was done by taking an identical gel lane containing all these bands and resolving them by SDS polyacrylamide gel electrophoresis in the perpendicular direction (data not shown). All bands that contain CCT subunits produce signals at their corresponding molecular weights. For example, any micro-complexes containing CCTα will yield a signal in the 57 kDa region after they are resolved by SDS-PAGE. In this manner, all bands observed on the non-denaturing gel lanes that were not comprised of CCT subunits were determined and were not considered during further analysis. However, all the signals that seem to represent bona fide CCT micro-complexes and which were superimposable provided the subunit association patterns.

For clarity, all the overlapping signals are indicated by inset arrows and each association between different types of subunit is indicated. In Table 1, all the observed subunit—subunit association patterns are tabulated.

Determination of the Subunit Orientation for the Torodial Ring in CCT

Analysis, based on the protein sequence of the CCT subunits and the structure of GroEL (Kim et al, Trends Biochem Sci. 19, 543–548, 1994), predicts that each type of CCT subunit will only associate to two other different types of subunit within each ring of CCT. As predicted, each type of CCT subunit associates only to one or two other different types of CCT subunit (Table 1) with the exception of CCTε which remains mainly as a free subunit. This feature of association specificity for each CCT subunit type suggests a unique orientation for the subunits forming the ring.

Figure 5:
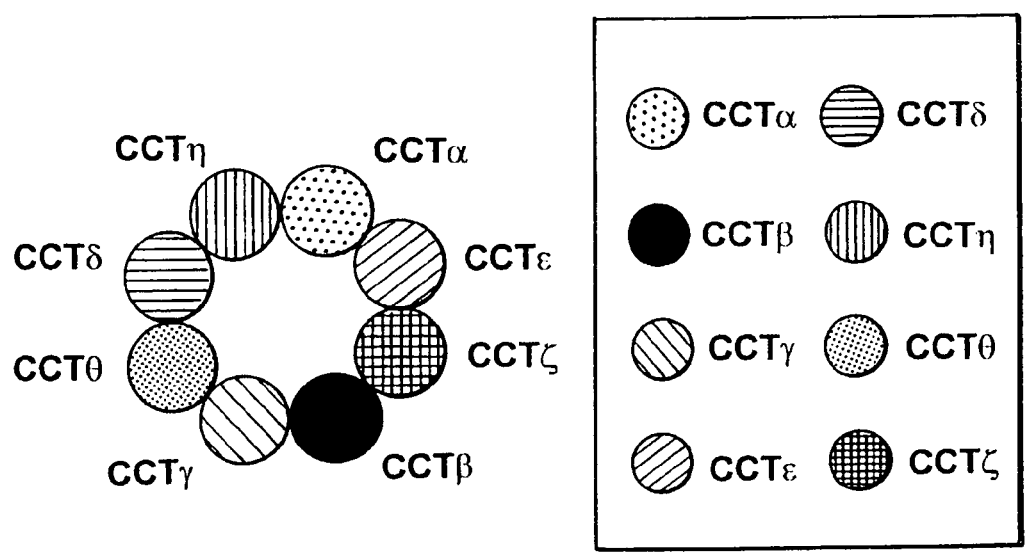
FIG. 5 shows the proposed CCT subunit orientation in each of the two stacked rings in CCT.

From Table 1, there are sufficient sets of association patterns to enable the construction of a probable subunit orientation within each CCT ring (FIG. 5). However, in mouse testis, the absence of an observable association pattern between CCTγ and CCTβ gives rise to an additional possible arrangement for the subunits in the ring.

TABLE 1

| | Subunit-Subunit Association Patterns observed in CCT Micro-Complexes | | | | | | | |
|---|---|---|---|---|---|---|---|---|
| | CCTα | CCTβ | CCTγ | CCTε | CCTδ | CCTθ | CCTη | CCTζ |
| CCTα | n.d | | | | | | | |
| CCTβ | – | n.d | | | | | | |
| CCTγ | – | +$^2$ | n.d | | | | | |
| CCTε | + | – | – | n.d | | | | |
| CCTδ | – | – | – | – | n.d | | | |
| CCTη | + | – | – | – | + | n.d | | |
| CCTθ | – | – | – | – | – | – | n.d | |
| CCTζ | – | + | – | + | – | – | – | n.d |

Figure 4:
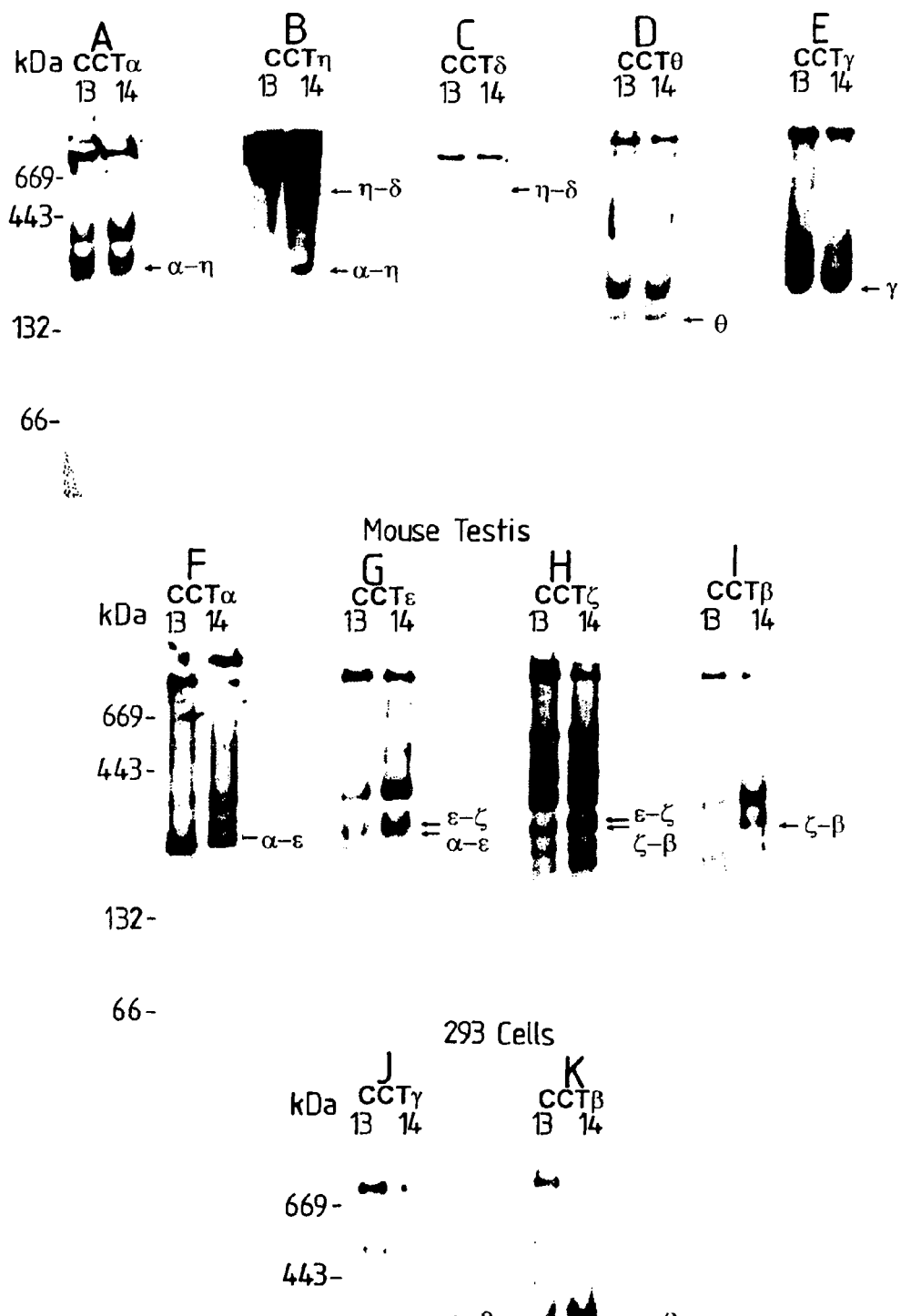
FIG. 4 shows mouse testis sucrose gradient fractions 13 and 14 (which correspond to sucrose density 1.054 g/cm$^3$ and 1.039 g/cm$^3$ respectively) analysed by non-denaturing polyacrylamide gel electrophoresis reveals the subunit—subunit association patterns in CCT micro-complexes. Sucrose gradient fractions 13 and 14 were resolved in a 6% non-denaturing polyacrylamide gel followed by Western blotting. The CCT subunit—subunit association patterns were determined by probing the blot sequentially with specific antibodies recognising the eight CCT subunits to locate superimposible bands. Panels A–E showed the distribution patterns of CCTα, CCTη, CCTδ, CCTθ and CCTγ respectively, when existing either as components of intact CCT or CCT micro-complexes or present as free subunits, on one Western blot. Panels F–I showed the distribution patterns of CCTα, CCTε, CCTζ and CCTβ respectively when existing either as components of intact CCT or CCT micro-complexes or present as free subunits on another equivalent Western blot. Panels J and K showed the distribution patterns of CCTγ and CCTβ respectively (as components of intact CCT or CCT micro-complexes as well as free subunits) in sucrose gradient fractions 13 and 14 of human 293 cells. Inset arrows indicate the corresponding superimposable protein bands and the symbols indicate the two subunit types whose association is inferred by this band e.g. The band α-η refers to the superimposible band on the blot when probed sequentially with specific antibodies recognising CCTα and CCTη respectively.

$^2$This association is not very clear in mouse testis but substantiated in Human 293 cells
n.d: Not Determined Nevertheless, the association of these two subunit types observed in human 293 cells (FIG. 4, panel J and K) allows discrimination between the two alternative arrangements from the mouse testis data. Analysis of sucrose gradients from cellular extracts by western blotting has proven the existence of the 920 KDa CCT complex comprising all 8 subunits in the double toroid structure. More detailed analysis across the sucrose gradient by western blotting with enhanced chemiluminescence has revealed the existence of many "micro-complexes" with lower molecular weights comprising monomeric, dimeric and trimeric combinations of the individual subunits. From extensive analysis of various tissues with antibodies to the individual subunits it is apparent that there are preferred or conserved combinations in these micro-complexes. Analysis of CCT subunit mutants in Yeast (Vinh and Drubin, Proc. Natl. Acad. Sci. USA. 91, 9116–9120, 1994) suggests that CCT subunit δ is implicated in actin binding, whilst CCT subunits α,β (Miklos et al, Proc. Natl. Acad. Sci. USA. 91, 2743–2727, 1994; Chen et al, PNAS. USA, 91, 9111–9115, 1994) are predominantly involved in tubulin binding. This is consistent with a unique structure whereby different substrate binding regions are spatially separated.

The existence of micro-complexes also suggests and supports the idea that individual or combinations of the CCT subunits might perform specific binding functions in their own right and that the CCT complex is a holding structure to enhance productive binding with substrate due to the higher regional concentration and geometry of subunits within the complex. If this is the case it would support earlier hypotheses that CCT and its individual subunits might perform significant control functions within the cell. Given the importance of CCT's substrates actin and tubulin and CCT binding partners cyclins D1, D2 and E in the function of the cell, it is equally reasonable to expect that CCT and its subunits may play pivotal control or checkpoint functions by binding to interactive regions of the substrates and binding partners.

As a direct result of discovering the existence of micro-complexes we have been able to fit a solution to the subunit organisation of the intact CCT complex. With 8 different subunits there are potentially 5040 combinations for a single toroid that might exist, however, by exhaustive analysis of the conserved micro-complexes there is only 1 solution to the CCT structure which satisfies the adjacent neighbour data disclosed. FIG. 5 portrays the subunit structure of one toroid of the intact CCT complex.

With the unique knowledge of this structure we expect the possibility of using the complex in soluble or immobilised form to probe for target BEPs and the possibility of using the intact CCT complex as a molecular vice, to hold recombinant or synthesised proteins for presentation to molecular probes that bind to folding intermediates held between known BEPs bound by interactions with, for instance, diametrically opposite binding subunits on the CCT toroid or even adjacent positions.

Differential Subunit Cycling Into the CCT Complex

Figure 6:
FIG. 6 shows the pulse chase analysis of CCT subunits and substrates. Germ cells were prepared from adult male CBA/Ca mice and 5×10$^7$ cells were labelled with 1mCi of $^{35}$S-methionine in 2.5 mls HEKRB for 1 house +/–a 4 hour chase with HEKRB+10 mM methionine. Post nuclear supernatants (PNS) were applied to 10.2–40% linear sucrose gradients, centrifuged at 25K rpm for 16 hours 4° C. in an SW28 rotor (Beckman) and collected as previously described (Lewis et al, 1992). 3% of the CCT 20S peak fractions were analyzed by 2D-PAGE (Hynes et al, 1995, 1996). Panels A and B shows analysis of a peak CCT fraction (19.8% sucrose) from the 1 hour pulse label by silver stain (A) and autoradiogram (B). Note that panel B is the same fraction as panel E in FIG. 1. Panel c shows an autoradiogram of the 20.4% sucrose CCT fraction from the 1 house pulse label followed by a 4 hour chase. The $^{35}$S-counts in each CCT subunit were measured by phosphorimaging. Counts in each CCT subunit were adjusted according to the predicted methionine content from the mouse cDNA sequence (Kubota et al., 1994, 1995b) and are expressed as a proportion of the counts observed in CCTε/S2=1. They are as follows; (1) Panel B: CCTθ/S1=0.24, CCTα/S3=0.9, CCTβ/S4=0.29, CCTγ/S5=0.29. (2) Panel C: CCTθ/S1=0.37, CCTα/S3=1.63, CCTβ/S4=0.64, CCTγ/S5=0.76, CCTζ2/S7=0.58. The efficacy of the pulse-chase conditions is demonstrated by the relative counts in α- and β-tubulin and CCTε in the pulse (Panel B; CCTε=1, α-tubulin=2.85 and β-tubulin=2.01) compared to the chase (Panel C: CCTε=1, α-tubulin=0.45, β-tubulin=0.28
Figure 6:
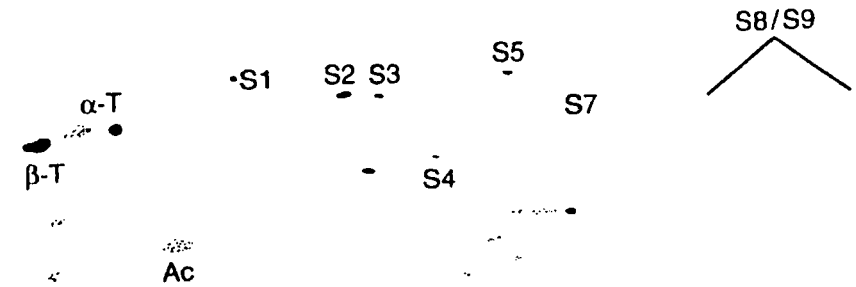
Figure 6:
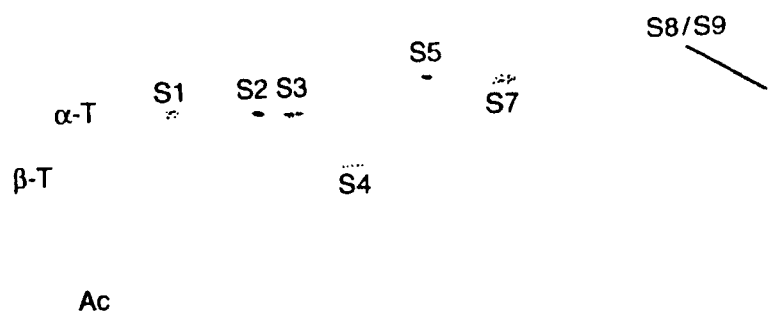

As discussed above, biochemical analysis of the CCT complex indicates that it has a unique subunit structure and composition. However, pulse-labelling with $^{35}$S-methionine of CCT complex in vivo appears inconsistent with this model because individual subunits do not label at similar rates and the following experiment provides quantitative data for supporting this hypothesis. Germ cell preparations were labelled for 1 hour with $^{35}$S-methionine and the 20S sucrose CCT peak (Lewis et al, Nature 358, 249–252, 1992) was analyzed by 2-D PAGE (FIGS. 6a, b). The present inventors have established a reference profile of the polypeptide composition of the 20S sucrose CCT peak using a combination of protein sequencing (Kubota et al, Curr. Biol, 4, 89–99, 1994), immunoblot analysis with antibodies to CCT subunits and substrates (Hynes et al, FEBS lett. 358, 129–132, 1995) and peptide mass fingerprinting (Hynes et al, Faseb J. 10, 137–147, 1996). The relative quantities of each CCT subunit observed by silver staining (FIG. 6a) and autoradiography are not equivalent (FIG. 6b); CCTα and CCTε (S2 & S3) have higher specific activities than the other subunits (normalized data in FIG. 6 legend) and CCTξ (S7) has very low specific activity. FIG. 6c shows CCT labelled for 1 hour as above, but followed by a chase in the absence of $^{35}$S-methionine for a further 4 hours. As expected, the substrates on CCT which are strongly labelled after a 1 hour chase period (FIG. 6b) have decreased activities after the end of the chase period (FIG. 6c); however, CCT subunits become more stoichiometrically labelled after the 4 hour chase. The combined data from these in vivo labelling experiments demonstrate that CCTα and CCTε, when incorporated into core CCT, are more heavily labelled compared to other subunits. This suggests that CCT subunits are in equilibrium between the main CCT complex and other pools of subunits and that, during the course of a 1 hour labelling period, the subunits of intact CCT must be turning over or cycling.

Further evidence of a complex and dynamic structure for CCT comes from this analysis of the rates and stoichiometry of CCT subunit synthesis. Were the CCT complex a unitary reactive folding centre akin to GroEL one might expect equivalent rates of synthesis of the individual subunits.

Analysis has revealed that in certain tissues there is a 5 fold range of mRNA levels between the various subunits and as a consequence of this there is a five fold range of labelling rate of the intact complex with $^{35}$S-labelled subunits. This data support the hypothesis of a highly dynamic fluxing CCT complex in which subunits and micro-complexes are constantly moving into and out of the "holding" complex in response to substrate binding, ring disassembly, ATP hydrolysis and reassembly.

Association of Individual Subunits on Microcomplexes After Complex Disassembly

The present inventors also observed that individual CCT subunits and/or CCT micro-complexes are generated from the disassembly process, which is consistent with the CCT micro-complexes detected in mouse testis lysate (Liou and Willison, EMBO J. 16, 4311–4316, 1997).

Semi Conservative CCT Ring Assembly

We have previously described an anti-mouse TCP1/CCTα monoclonal antibody, 23C (Willison et al, Cell. 57, 621–632, 1989) which fails to bind human TCP-1 (Lewis et al., 1992) and TCP-1 of other primates and *Xenopus laevis* (Hynes et al, Faseb J. 10, 137–147, 1996). All mammalian TCP-1 genes sequenced so far contain 556 residues and are 96% identical with mainly the extreme N and C-termini showing a significant degree of sequence divergence between species. The 23C monoclonal antibody binding site on mouse TCP-1/CCTα has been mapped to an epitope 'LDD' which is situated as the last three residues of the mouse CCTα. The reason for the absence of binding of 23C to a single residue change in the 23C epitope region in human TCP-1, D555N (Harrison-Lavoie et al, EMBO. J. 12. 2847–2853, 1993; Hynes et al. Faseb J. 10, 137–147, 1996), making the last three residues as 'LND'. In the case of rabbit CCTA, we ascertained that the last three residues were 'LLD' by PCR amplification of a rabbit brain cDNA library (FIG. 8).

Subsequently, a D555N mutation was introduced into mouse CCTα to remove the 23C antibody binding site giving rise to a mutant encoding mouse CCTα with 'LND' as the C-terminal end. Consequently in rabbit reticulocyte lysate, rabbit CCT should bind to 2 molecules of 23C and if the rabbit CCTα is exchanged for the corresponding mouse CCT subunit by its expression in vitro, the labelled CCT should still bind 2 molecules of 23C. If however, the LND mutant CCTα is expressed and incorporated into rabbit CCT, there are two possible outcomes with respect of 23C binding depending on the mechanism in play. If there is complete disassembly and reassembly of CCT, all the newly assembled labelled CCT should contain 2 'LND' CCTα subunits. However, if the assembled labelled CCT contains only a single 23C binding site, then there must be single ring disassembly and reassembly.

Figure 8:
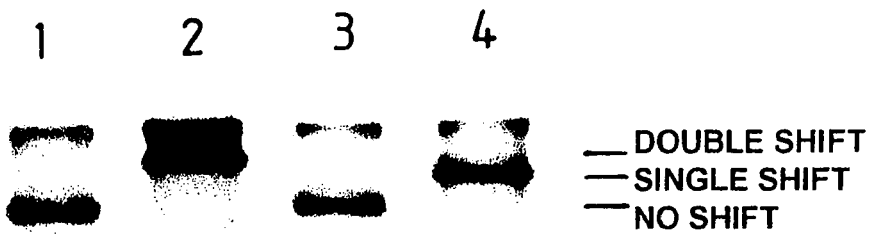
FIG. 8 shows newly synthesized CCT subunits are incorporated into CCT semi-conservatively. (A) The protein sequences of the C-termini of rabbit (SEQ ID NO: 16), wildtype (SEQ ID NO: 16) and mutant mouse CCTα (SEQ ID NO: 17). (B) The difference in CCT migration distance induced by monoclonal antibody 23C after incorporating either wildtype mouse CCTα (lane 2) or mutant CCTA (lane 4) is clearly discernable. Lane 1 and 3 represents the migration of CCT without exposure to antibody 23C after incorporating either wildtype mouse CCTα (lane 1) and mutant mouse CCTα (lane 3). (C) A pictorial representation of the coupling of two antibody molecules onto rabbit endogenous CCT and one antibody molecule coupled onto CCT containing an incorporated mutant mouse CCTA subunit (subunit in black).
Figure 8:
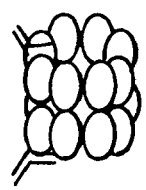
Figure 8:
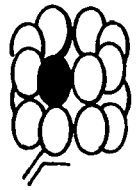

By introducing antibody 23C into a rabbit reticulocyte lysate mix containing expressed mouse CCTα, the presence of a shift in migration distance of CCT is observed (FIG. 8, lanes 1 and 2). However, when the D555N mutant mouse CCTα is expressed, the retardation of CCT migration was only half of that observed with wildtype mouse CCTα (FIG. 8, lane 4). This lessening of shift to half the migration distance is attributable to a single antibody molecule only being coupled onto CCT. This result implies that the incorporation of CCTα is one ring at a time at every reassembly cycle. A pictorial representation of the endogenous CCT coupled with two antibody molecules of 23C and mutant CCT coupled only to one antibody molecule of 23C is shown in FIG. 8. In summary, this result indicates that the incorporation of subunits into CCT occurs singly. By extrapolation, the disassembly process is also expected to occur in single ring fashion, meaning that only the ring that was occupied by the substrate is disassembled during the folding cycle.

Use of CCT Complexes to Identify Immobilised Binding Epitope Peptides (BEPs) on CCT Substrates Prior art has shown that certain domains within substrate proteins are responsible for the interaction with CCT. Dobrzynski et al have defined an internal M domain in β-tubulin spanning some 120 amino acids which interacts strongly with TRiC and a further 140 "N" terminal amino acids which interact less strongly with TRiC. Previously one might have expected that large tracts of proteins generally representing the hydrophobic core of soluble proteins are responsible for the interaction with chaperonins, unexpectedly in this embodiment we find that small peptides spanning 15 residues are capable of high affinity binding to CCT complexes. Further the present inventors have discovered that there are numerous binding sites along substrate molecules, identifying what we term binding epitope peptides (BEPs) or binding members and that there are specific clusters of BEPs along the substrate molecule. By panning the entire substrate molecule, in this case actin, in 15 residue portions, the present inventors have identified not only BEPs but also hot spots or clusters where there are clearly enlarged epitopes which encompass 30–40 residues of high affinity binding.

Peptides of 15 amino acids in length were synthesised on polyethylene pins mounted on blocks according to the method of Maeji et al (Maeji N. J. et al, 1994) and commercially available under the trade name of Pepsets™ from Chiron Mimotopes. The sequence of the peptides were such that they defined the full length of the actin sequence with a 5 amino acid overlap between the sequential peptides, and selected peptides representing key known structures in actin (Table 2 annotated). The peptides are synthesised on polyethylene pins which are presented to be compatible with standard 96 well microtitre plates. The pins become the solid phase on which interactions with CCT complexes can be probed. The method is described below.

1. Take Pepset pins from storage at −20(° C.) and equilibrate at room temperature.
2. Wash pins with PBS for 10 minutes at room temperature on a shaking table.
3. Incubate pins with blocking buffer (2% w/v BSA 0.1% Tween 20 in PBS) for 60 minutes at room temperature on a shaker.
4. Wash pins with PBS for 10 minutes at room temperature on a shaker (times 1)
5. Take 20S mouse testis sucrose gradient fractions enriched in CCT and make up to a volume of 100 ml with binding buffer (0.5 mM MgCl$_2$ in breaking buffer pH7.2)
6. Incubate pins with CCT solution overnight at 4° C. on a shaker
7. Continue incubating the pins at room temperature with the CCT solution for one hour at room temperature on a shaker.
8. Wash pins with PBS for 10 minutes at room temperature on a shaker (times 3).
9. Incubate pins with a solution of 91a, monoclonal antibody to CCTα, (5 ul of Affinity Bioreagents stock 91a in 100 ml of PBS) for 2 hours at room temperature on a shaker.
10. Wash pins with PBS for 10 minutes at room temperature on a shaker (times 3).
11. Incubate pins with anti-rat CAP (Pierce product No. 31350) (5 ul in 100 ml PBS) for 2 hours at room temperature on a shaker.
12. Wash pins with PBS for 10 minutes at room temperature on a shaker (times 3).
13. Dispense 200 ul pNPP liquid substrate (Sigma product No. N7653) into each well of a 96 well microtitre plate (Immulon product No. M129A11-50).
14. Invert pins into microtitre plate and incubate with pNPP reagent for 30 minutes at room temperature in the dark.
15. Remove pins from the microtitre plate and read the microtitre plate at 410 nm on a Dynatech ELISA plate reader.
16. Results are expressed as a 410 nm absorbance reading for each well corresponding to each unique substrate peptide from the actin molecule.

Figure 9:
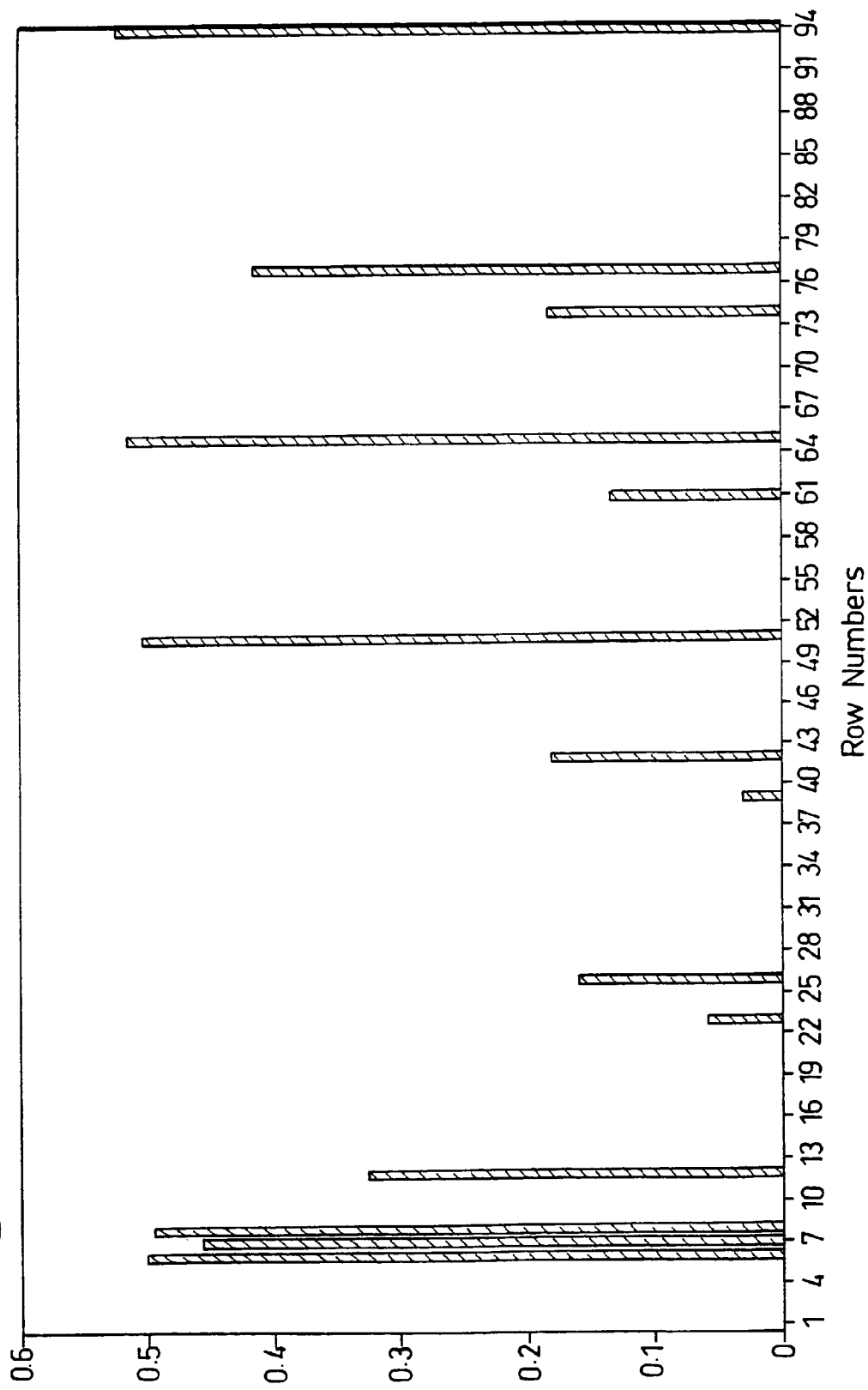
FIG. 9 shows the 410 nm absorbance reading obtained versus the substrate peptide number for the actin molecule as shown in Table 2.

FIG. 9 Shows the 410 nm absorbance reading obtained versus the substrate peptide number for the actin molecule; unexpectedly there are unique hot spots of binding along the actin molecule which define the binding epitope regions for CCT. The sequence of the BEPs for actin are displayed in Table 2 and show that the BEPs for actin are not exclusively comprised of hydrophobic peptides but a mixture of hydrophilic and hydrophobic peptides with differing charges. This suggests that these BEPs are unique binding sites for CCT which are highly specific and probably bind to differing subunits of CCT or differing regions on individual CCT subunits. Further the hot spot of BEPs situated at substrate peptides 6–8 is (FIG. 9) the major surface binding region of actin for DNAse 1 clearly showing that CCT; i) does not exclusively bind to hydrophobic inner cores like GroEL; ii) binds to surface residues accessible to aqueous solution; and iii) binds to regions of proteins implicated in non-CCT protein—protein interactions of significance in intracellular processes. Further, there appears to be two or three types of interaction site or epitope as gauged by the strength of CCT binding to the immobilised peptides; primary sites, reference peptide numbers 1, 2, 3 4 and 5 (FIG. 10); secondary sites, reference peptides 6, 7 and 8 (FIG. 10); and tertiary sites, reference peptides 9, 10, 11, 12, 13, 14 and 15 (FIG. 10). These may truly represent secondary or tertiary interaction sites or may be equally strong binding epitopes that are conformationally restricted or cleaved during the immobilisation process. Such secondary or tertiary interaction sites should be probed in alternative procedures to determine the strength of binding to CCT.

If CCT's role within the cell is to prevent unscheduled interactions between proteins that are folding or merely residing as intracellular pools, then it is reasonable to assume that key interactive sites of proteins such as actin, tubulin and even the cyclins will be recognised by CCT to prevent such non productive interactions. The experiment described above has an internal positive control in the major DNAse 1 binding site which is one of the major binding sites for actin. The methodology described has indeed identified a major protein—protein interaction site on actin, but unexpectedly has also identified a new protein interaction site in peptide 61 (FIG. 9) the role of which has yet to be elucidated. The present inventors anticipate therefore that the methods described will enable hitherto unrecognised sites of modulation and protein—protein interaction to be identified on CCT substrates and binding partners.

Immobilised BEPs Identified by CCT are Also Recognised in Free Solution

Figure 11C:
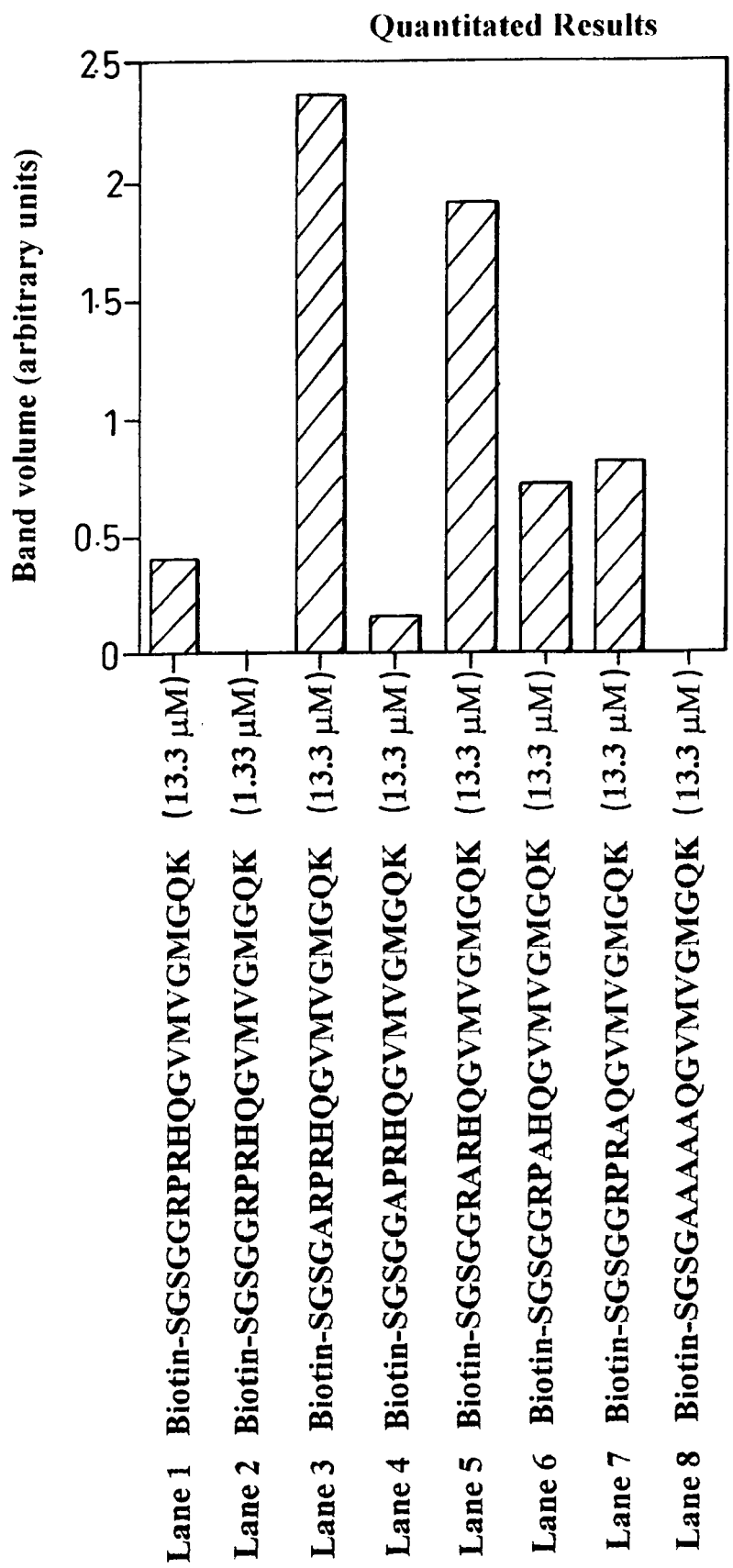
FIG. 11C shows the results quantitated.

The molar concentration of BEP immobilised on the pin used in the screening assay is extremely high and potentially may have no relevance to the interaction between the actin molecule and CCT in the cytosol. Therefore the present inventors incubated CCT with biotinylated (biotin plus SGSG linker attached at the N-terminus) actin peptide number 8 (FIG. 11) in buffered solution and then subjected the complete mixture to non denaturing gel electrophoresis which separates the non-binding peptides from CCT-bound peptides. The gel was western blotted and probed with streptavidin-HRP conjugate to determine the position of the biotinylated peptides (FIG. 11). The biotinylated peptide number 8 (FIG. 11) was shown to co-migrate with the CCT complex, whereas control peptides did not. This verifies that significant and specific binding between CCT and BEPs identified in the immobilised assay occurs in free solution.

A further analysis was performed with derivatives of peptide 8 (FIG. 11) wherein alanine substitutions were made within the peptides (8.1, 8.2, 8.3, 8.4, 8.5, 8.6) to try and further identify the critical residues responsible for CCT binding (FIG. 11).

The present inventors have found that substitution of the sequence GRPRH (SEQ ID NO: 121) by sequential alanine residues within peptide 8 significantly depletes or enhances binding to CCT in this free solution assay (FIG. 1/c). This further confirms the ability of the methodologies embodied herein to identify protein—protein interaction sites, to find the minimal number of residues responsible for binding within a BEP and to perform mutation analysis on the BEPs to modify the efficacy of BEP binding.

The positive BEPs identified in the immobilised assay also bind with significant affinity in free solution, supporting the premise that these peptides do indeed represent "binding epitopes" of relevance in the cytoplasmic setting.

Inhibition of Substrate Binding to CCT by BEPs

For BEPs identified for various CCT substrates to be of any use they must efficaciously compete with native or folding polypeptide for occupancy of the CCT complex, CCT micro-complex or CCT subunit. A simple competition assay has been developed whereby an actin BEP is incubated with CCT complex (Ha-Ras-β-Actin site II mRNA containing amino acid residues 178–262 of β-actin fused to the C-terminus of human Ha-Ras amino acid residues 1–166) primed rabbit reticulocyte lysate to determine if BEPs can inhibit productive binding between newly synthesised Ha-Ras-β-Actin site II protein and CCT. Peptides from residues 178–262 of β-actin containing six of the BEPs (FIG. 9) resulted in inhibition of binding to the CCT complex.

Micro-Injection of BEPs Into Living Cells has Profound Physiological Effects

Previous studies have shown that injection of antibodies to CCT into living cells has a profound effect on microtubule mediated events (Brown et al, J. Biol. Chem. 271, 824–832, 1996), in this case centromere function was profoundly disrupted as a result of the inability of CCT to assist in the folding of tubulin. This work suggests that CCT is critically implicated in centromere function whereas another chaperone hsp73 is less critical in this setting, since microinjection of anti-hsp73 antibodies did not illicit the same response as anti-CCT antibodies.

BEPs isolated from actin when injected into cells will have a significant effect on actin mediated events such as membrane ruffling and other cellular motion events mediated by the actin cytoskeleton. The BEPs will compete with newly synthesised actin for binding to CCT which will result in incomplete folding of actin thereby disabling the cell from assembling native actin that has been newly synthesised.

Therapeutics Based on BEPs

The unexpected discovery that substrate proteins for CCT possess restricted multiple hot spots of binding which correspond to critical regions of protein—protein interaction has significant implications on the design of new therapeutic molecules for many diseases.

The CCT BEPs identified on the actin molecule represent highly specific "epitopes" of protein—protein interaction which are distinctly different to the tracts of hydrophobic amino acids which characterise the non-specific binding regions for GroEL and its substrates. This observation supports other data which shows that GroEL will bind to most denatured proteins whereas (Viitanen et al, Protein. Sci. 1, 363–369, 1992) many denatured substrates will not bind to CCT (Melki and Cowan, Mol. Cell. Biol, 14, 2895–2904, 1994). This suggests that the interaction between CCT and its substrates is more specific and may be responsible for a control function in cellular physiology.

Some 5–10 BEPs on actin have been identified using the methodologies disclosed above and the amino acid composition of these BEPs shows that, unlike folding cores for model proteins such as Barnase which are predominantly hydrophobic and indeed non-specific, the BEPs for actin are equally mixed hydrophobic and hydrophilic peptides. The present inventors anticipate that in the design of therapeutics the BEPs identified by the disclosed methods may need significant optimisation to elicit stronger binding. The embodiment herein also discloses the concept of using antibodies against the initial BEPs to screen peptide libraries, whereby the anti-BEP antibody replaces CCT, CCT microcomplexes or individual CCT subunits in the screening assays to seek stronger more potent binding partners for CCT.

The unexpected finding of relatively small binding epitopes on CCT substrates suggests that CCT might be used to identify regions on substrate proteins which are involved in protein—protein interactions other than with CCT. Whereas those skilled in the art use panels of monoclonal antibodies or degenerate peptide libraries to identify protein—protein binding sites on known interacting proteins, the methodology described herein offers the potential to identify protein—protein interaction sites between the CCT substrate molecule and other unknown proteins by virtue of identifying the BEPs for CCT binding. Protein sites that bind strongly to CCT are obvious candidates for binding to other proteins and furthermore may not be obvious binding sites if they are buried in the native state. Since CCT recognises folding intermediates and indeed CCT micro-complexes remain bound to folding intermediates after CCT disassembly, it is reasonable to assume that BEPs for CCT may represent conformational epitopes not normally available for solution phase binding to the native protein, being only available after conformational changes to the protein.

Not only do the present inventors anticipate identifying new protein-peptide therapeutics using the BEP panning methodology described above but also therapeutics which are specifically designed to target actively synthesising cells. BEPs which are identified as binding to CCT will compete with newly synthesised polypeptides for CCT binding rather than existing pools of CCT substrates. This is a significant advantage over drugs which interfere with tubulin by stabilising or disrupting the microtubules.

Inevitably for anti-tumour drugs there is significant toxicity associated with their use since all cells will be susceptible to drugs such as taxol and vincristine that stabilise microtubules and it is only by virtue of the fact that actively dividing cells require constant turnover of microtubules to achieve replication that tumours are marginally more susceptible than normal tissue. The present inventors therefore anticipate that BEP, BEP mimics and small molecules that compete with BEP binding to CCT will represent novel therapeutic candidates which will target cells active in protein synthesis, since inhibitors of BEP binding to CCT are specific for substrate proteins that are folding after synthesis, rather than existing pools of folded CCT substrates.

New Substrates for CCT Binding

Figure 12:
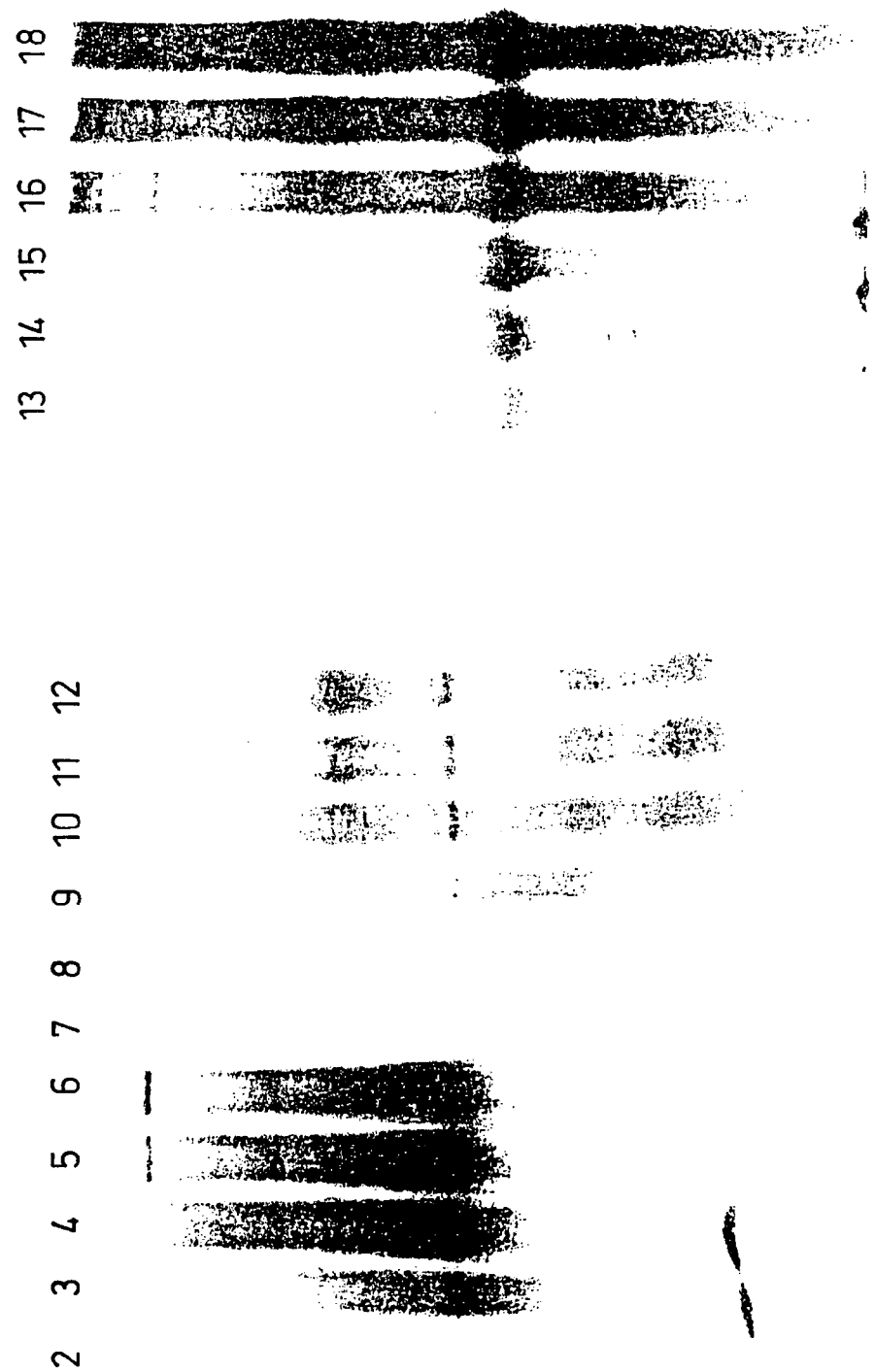
FIG. 12 shows the interaction of cyclin D1 and cyclin E with CCT. p Bluescript plasmids containing full length mouse-cyclin D1 cDNA or human cyclin E cDNA were used to programme rabbit reticulocyte lysate transcription translation systems (Liou & Willison, EMBO J. 16, 4311–4316, 1997). Time courses of interactions of cyclins with CCT were analysed on 6% native polyacrylamide gels (Liou & Willison,EMBO J. 16, 4311–4316, 1997). At the indicated times, 5 μl aliquots of the lysate reactions were added to 7 μl of f10 ml EDTA (ph 8.0) and 4 μl of 4× gel loading buffer and placed on ice. The lanes 1–6 show CCT a at t=0, 5, 10, 20, 30, 60 minutes. Lanes 7–12 show pBSK CY1 1 (mouse D1) at t=0, 5, 10, 20, 30, 60 minutes. The right hand panel (lanes 13–18) shows a time course expression of cyclin E at t=0, 5, 10, 20, 30, 60 minutes. In the right hand panel, the lane marked M shows the migration of molecular weight markers of 886 kDa and 43 kDa. This kinetic analysis shows that cyclins do not appear to be interacting with CCT in a manner resembling bone fide substrates, such as actins and tubulins, but seem to have similar kinetics as the cycling of CCT subunits into rabbit CCT in the lysate. This suggests some regulatory role for the interactions of cyclins with CCT.
Figure 13:
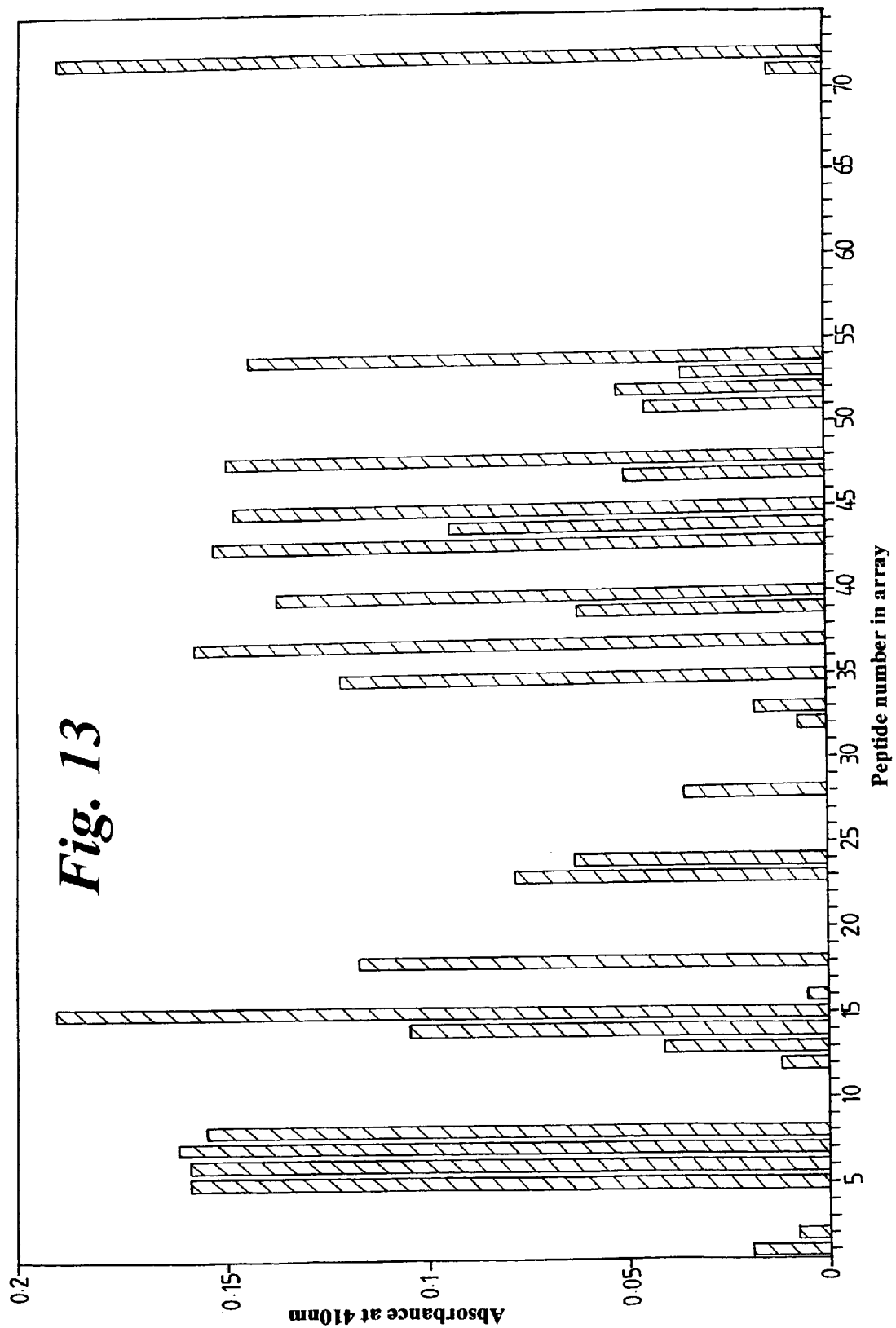
FIG. 13 shows in graphical form the absorbance at 410 nm for the peptides as illustrated in Table 2 in order to show that actin makes contacts with isolated CCTδ subunit apical domain.

It is well reported in the literature that the known substrates for CCT are actin and α, β and γ tubulins. Accordingly BEPs identified for these known CCT substrates are obvious candidates for the identification of new therapeutic candidates. The present inventors have already disclosed in the prior art that there are many other unknown substrates that specifically bind to CCT at the time of their synthesis. The present inventors now disclose that Cyclin E, D1 and D2 are specific binding partners for CCT with binding kinetics which are significantly different to kinetics for folding substrates such as actin or tubulins (FIG. 12). This is significant in that specific binding partners have been identified that bind in a manner not concomitant with folding but which nevertheless bind specifically. This opens up the possibility that protein binding to CCT, CCT micro-complexes or CCT subunits or active portions thereof could act as a control mechanism preventing binding to other non-CCT subunits therefore placing CCT in a pivotal control function for cellular processes. The data provided by the present invnentors here on BEPs from actin showing that a major binding epitope is the surface positioned major binding region for DNAse 1 confirms that BEPs for CCT are likely to be significant interaction points for protein—protein interaction with non-CCT proteins. Therefore, the present inventors anticipate the identification of BEPs for these proteins and subsequently peptide, peptide mimetics, antibodies, antibody fragments and small molecule inhibitors of CCT binding that cause therapeutic effect through interaction with Cyclin E, Cyclin D1 and D2 directly or by competing with their binding with CCT and other cellular proteins.

Mutation of β-Actin Site I

The present inventors have focused their attention on β-Actin Site I, a high-affinity site which occupies three overlapping peptides and spans amino acid residues 26–50 of actin subdomain 2. They demonstrated the interaction between CCT and N-terminally biotinylated peptide in solution. CCT and peptide corresponding to β-Actin Site I (FIG. 10, peptide 8) were incubated together and the reactions were then electrophoresed on native PAGE gels, western blotted and probed with streptavidin-Horse Radish Peroxidase (HRP). A biotin signal co-migrating with CCT was detectable within a 10-fold concentration range of peptide (1.33 μM to 13.3 μM) and fixed concentration of CCT (70 nM). Five alanine-scan point mutations across the core sequence ($^{36}$GRPRH$^{40}$; SEQ ID NO: 121) of β-Actin Site I were screened for effects on interaction with CCT. The mutant peptides showed equivalent, reduced or enhanced binding, but not absence of binding, although replacement of all five residues of the GRPRH (SEQ ID NO: 121) core sequence by AAAAA (SEQ ID NO: 122) resulted in abrogation of binding to CCT. The inventors noted that the act1-132 mutant allele of the yeast actin gene, ACT1, which contains a double alanine replacement in the core, $^{36}$GAPAH$^{40}$(SEQ ID NO: 123), has a recessive Cs$^-$, Ts$^-$ phenotype in vivo (Wertman et al, Genetics 132, 337–350, 1992).

In Vitro Interaction of Isolated CCT5 Apical Domain with β-Actin Site I

Since β-Actin Sites I, II and III are widely separated in the actin structure, it seemed likely that actin is contacted by more than one CCT subunit apical domain, considering that the dimensions of the barrel-shaped CCT are 16×15 nm (height×diameter) (Llorca et al, J. Biol. Chem. 273, 1–4, 1998) and actin monomer is a half-cube (6×6×3 nm). Native actin monomer can be placed into the cavity of the archaebacterial CCT homologue, the α/β thermosome (15.8×16.4 nm, height×diameter), in computer modelling experiments, suggesting that, not only could β-actin be accommodated in the cavity, but that it might bind to the apical domains of more than one CCT subunit. (Ditzel et al, Cell 93, 125–138, 1998)

In order to test the idea that actin makes multiple contacts with CCT subunits, the apical domain of the CCTδ subunit, expressed in and purified from E. coli, was tested for interaction with the β-actin peptide array. CCTδ apical domain, double tagged at the C-terminus with a –GALDD pentapeptide, to allow detection with MAb, 23C [Harrison and Lavoie, EMBO J. 12, 2847–2853, 1993) and with a His$_6$ motif to allow detection with MAb HIS-1 (Sigma). CCTδ apical domain interacts strongly with β-Actin Site I, but not with other peptides which show ATP-dependent interaction with the CCT holochaperonin; in particular, peptides within β-Actin Site III (FIG. 14), which suggests specificity of interaction of individual CCT apical domains with discrete regions of actin.

In vivo Selected Mutation in CCT4/δ Apical Domain

Since the inventors found an interaction between purified mouse CCTδ apical domain and β-Actin Site I peptides, they decided to determine the complete DNA sequence of the anc2 -1 mutant allele of the Saccharomyces cerevisiae CCT4 gene encoding the δ subunit of CCT, since the present inventors surmised that it might have suffered an alteration in its apical domain because of the manner in which the anc2-1 mutant was isolated. Briefly, anc2-1 was recovered in a screen for extragenic mutations that fail to complement temperature-sensitive alleles of the single yeast actin gene ACT1, hence, actin-non-complementing (Welch et al, Genetics 135, 265–274, 1993). Anc2-1 exacerbates the phenotype of the semi-dominant, temperature-sensitive actin allele act1-4 (Glu259Val) and other mutations within subdomain 4 of actin. However, what excited the present inventors was that anc2-1 complements actin alleles act1-1, act1-2, act1-122, act1-124 and act1-125, and these five mutations lie on either side of β-Actin Site I in ACT1. The wild-type CCT4 and mutant anc2-1 genes were fully sequenced by direct cycle sequencing of PCR fragments of genomic DNA and a single nucleotide change was found between them (G–A) which changes Gly 345 to Asp. This glycine residue lies on a β-strand found on the outside surface of the globular part of the Type II thermosome apical domain and is conserved in all chaperonins (Klumpp et al, Cell 91, 1–20, 1997). Since substrate is thought to interact with the surface of the apical domain facing the cavity (Fenton et al, Nature 371, 614–619, 1994), (Xu, X. et al, Nature 388, 741–750, 1997) (Ditzel, L. et al, Cell 93, 125–138, 1998), it is likely that anc 2-1 Gly 345 Asp has altered properties in the movement of the apical domain required for binding and/or release of substrates, rather than in direct interaction with substrate. This interpretation is consistent with the phenotypes of diploid yeast strains which contain wild-type and mutant copies of both actin and Cct4p proteins (Vinh, D. B. N. et al, PNAS U.S.A. 91, 9116–9120, 1994), (Vinh, D. B. N. et al, Genetics 135 275–286, 1993), since the chaperonin complexes containing a mutant Cct4p subunit must still be able to provide effective interaction with wild-type actin folding intermediates in addition to increasing the yield of functional mutant actins. It is clear from Table 2 of Vinh and Drubin (PNAS U.S.A. 91, 9116–9120, 1994) that in vivo aggregates of act1-1p, which do not stain with phalloidin, suggesting that the actin is misfolded, are reduced by anc2-1 function. Furthermore, we note that the act1-132 allele, which contains a double mutation, R37A and R39A (Wertman K. F., et al, Genetics 132, 337–350, 1992), in the core of β-Actin Site Ia, grows very poorly as a haploid at all temperatures. Nevertheless, act1-132 is recessive in diploids with ACT1, suggesting that actin filament function is not seriously perturbed upon incorporation of mutant act1-132 protein; it is possible that act1-132 protein is defective by virtue of impaired interaction with CCT.

GroEl and CCT Interact With the Same Sites on β-Actin

In vitro refolding experiments have shown that Group I chaperonins can bind to denatured actin with high affinity, and release it in response to ATP incubation. However, actin released from GroEL/Hsp60 does not appear ever to be able to attain native state. The present inventors have investigated which sequences in the β-actin peptide array were bound to *E. Coli* GroEL using an assay similar to the one developed for CCT. The array was incubated in the presence of chaperonin but with no nucleotide and bound GroEL was detected by a monoclonal antibody, Mab 4-3F. GroEL recognizes the same peptide sequences that CCT does but recognises serveral others in addition, and thus GroEL appears to be able to discriminate between peptide sequences less well. GroEL binds many peptides with apparent high affinity to give maximum signals under these assay conditions (FIG. 15) As for CCT, most of the GroEL-reactive peptides are located on the surface of the native protein.

Interaction Between β-Actin and CCT Requires Co-Operative Binding Sites on Actin Upon in vitro translation of actin mRNA in rabbit reticulocyte lysate, several truncated forms of $^{35}$S-actin are captured by and accumulate on CCT. This is also the case for α-tubulin (Liou, K. F., et al, Biological Chem. Hoppe-Seler 379, 311–319, 1998). The present inventors showed by immunoprecipitation with monoclonal antibodies recognizing either the C-terminus or the N-terminus of actin, that the truncated forms all contain intact C-termini, but none contains N-termini. Thus, the actin is fragments are not ribosome released nascent chains, but are the consequence of initiation of translation at internal methionine residues in actin, and a comparison of the experimentally determined molecular weights of the truncated forms with the sequential occurrence of the methionines in mouse β-actin supports this interpretation. This result maps a major CCT interaction site in β-actin to the left-hand site of the nucleotide binding (standard front view of actin (Kabsch W. et al Nature 347, 37–44, 1990) cleft made up from subdomains 3 and 4 (residues 150–375), and demonstrates that actin can interact with CCT in the absence of β-Actin Site I. Furthermore, it seems as if co-operative interaction is required for productive interaction between CCT and actin, because the truncated products, 3 and 4, are not released efficiently but accumulate 20–30-fold over 70 minutes compared with full-length β-actin and truncated product 1, which contains β-Actin Site I. However, no IVT products smaller than 29 kDa were immunoprecipitated by the MAb to the C-terminus of actin. Therefore, no fragments smaller than 29 kDa are produced by internal initiation in the IVT reaction.

Fusion of Actin Domains Targets Ha-Ras to CCT

The existence of discrete CCT binding sites on actin and the co-operative nature of their interactions with chaperonin suggests that β-actin attains a degree of tertiary structure before it is competent to interact with CCT. Actin is an impressively plastic molecule with numerous protein binding sites which can appear and disappear depending upon the nucleotide, divalent cations and actin binding proteins which are bound. It occurred to the present inventors that the critical step in folding could be the successful occupancy of the nucleotide binding site by ADP or ATP. The form of actin which interacts with CCT could therefore be a collapsed state with no nucleotide occupying the cleft between the left and right domains. The inventors predicted that there should exist a relaxed domain which binds a single CCT site and then begins the development of a second tense site by allosteric communication which appears elsewhere on the folding intermediate. This could result in actin being held by two regions on either side of the cleft and allow the diffusion of nucleotide into the site. The following experiments are consistent with this model.

Figure 7:
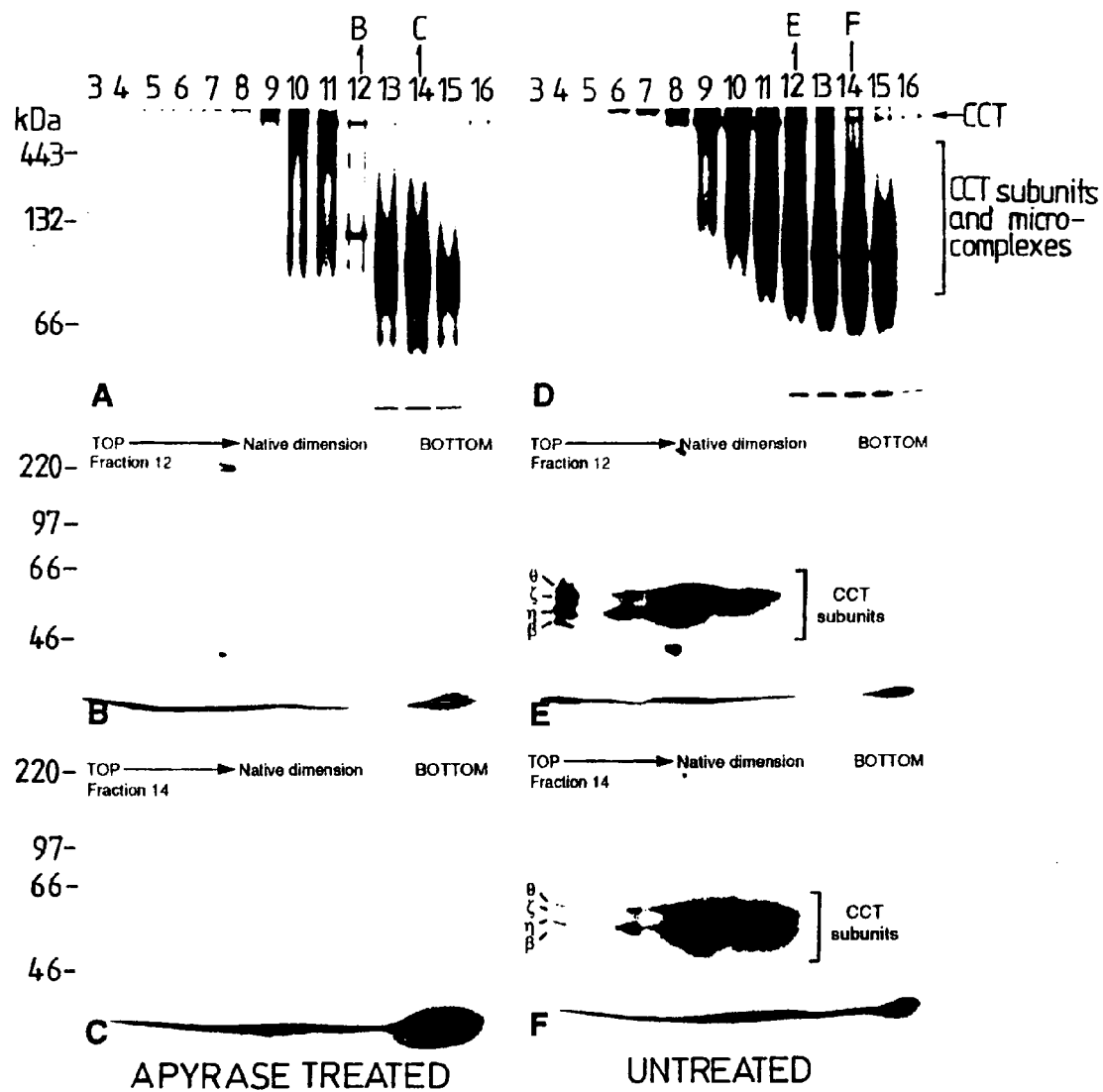
FIG. 7 shows ATP Dependence of CCT Disassembly in Reticulocyte Lysate. The ring disassembly of $^{35}$S-labelled CCTβ, CCTζ, CCTη and CCTθ containing CCT, into CCTβ, CCTζ, CCTη and CCTθ micro-complexes and/or CCTβ, CCTζ, CCTη and CCTθ monomers monitored by sucrose fractionation and 6% non-denaturing PAGE (A and D). Chosen light sucrose fractions (fractions 12 and 14) which contain free CCT subunits and/or CCT microcomplexes were also analysed by SNaDE (B, C, E and F). (A) ATP-depleted reticulocyte lysate, reconstituted with CCT, labelled with CCTβ, CCTζ, CCTη and CCTθ. The reaction mix was separated along a continuous 10–40% sucrose gradient and the resultant fractions 3–16 were resolved in a 6% non-denaturing polyacrylamide gel. The distribution of labelled CCT subunits were determined by autoradiography. (B) and (C) Analysis of sucrose fractions 12 and 14 respectively from (A) by semi-native diagonal electrophoresis to illustrate the absence of ring disassembly of CCT in the presence of apyrase. Samples from fractions 12 and 14 were resolved by 6% native PAGE followed by 8% SDS PAGE in the perpendicular direction. Only contaminating protein signals were observed by autoradiography. (D) Untreated reticulocyte lysate, reconstituted with CCT, labelled with CCTβ, CCTζ, CCTη and CCTθ, was separated along a continuous 10–40% sucrose gradient with the resultant fractions 3–16 resolved in a 6% non-denaturing polyacrylamide gel. The distribution of labelled CCT subunits was determined by autoradiography. (E) and (F) Analysis of sucrose fractions 12 and 14 respectively from (D) by semi-native diagonal electrophoresis to illustrate the ring disassembly of CCT since signals representing CCT subunits or micro-complexes were present in both fractions (arrowed).

The present inventors made fusion proteins which linked β-Actin Site I (residues 31–70) or Site II residues 178–262; 6 of the peptides (Table 2) are located in this segment) containing fragments to the C-terminus of Ha-Ras (residues 1–166). Ha-Ras is a single domain GTP-binding protein whose structure (residues 1–168) has been determined at high resolution (Wittinghofer, A. et al Trends in Biochem. Sci 16, 382–387, 1991). The Ha-Ras-β-Actin Site I fusion proteins do not interact strongly with CCT upon in vitro translation in reticulocyte lysate (FIG. 7b). Various other fragments of this region of actin, between residues 1–70, and fusion to the NH$_2$-terminus rather than the C-terminus, of Ha-Ras were tested with similar results (data not shown). Furthermore, these Ha-Ras-β-Actin Site I fusion proteins do not interact with DNase I, suggesting that this isolated domain cannot attain the tense state required for induced fit binding of the surface loop to DNase I (Kabsch W. et al Nature 347, 37–44, 1990). However, Ha-Ras-β-Actin Site II fusion proteins do interact with CCT. It is probable that actin folding intermediate interaction with CCT requires co-operative interaction between sites on either side of the nucleotide-binding cleft. The present inventors suggest that the first sites to bind CCT are β-Actin Sites II and III, located in subdomains 3 and 4 of actin. Upon binding of β-Actin Sites II and III to CCT, a conformational change is induced in subdomain 2 of actin, which allows β-Actin Site I to be captured by CCT.

Purification of Isolated CCT5 Apical Domain

CCTδ apical domain (residues D219 to N394 tagged at the C-terminus with a (His)$_6$ motif followed by a GALDD pentapeptide) was cloned into pET11d vector (Stratagene), transformed into BL21 (DE3) pLysS competent cells (Stratagene) and induced to OD=0.8 for 3 hours at 30° C. with 1 mM IPTG. The cell pellet from 250 ml culture was resuspended in lysis buffer (50 mM NaH$_2$PO$_4$, 10 mM Tris, 100 mM NaCl, 1% Triton X-100, 5 ug/ml chymostatin, 10 ug/ml. leupeptin, 5 ug/ml antipain, 5 ug/ml pepstatin A [pH8.0]), sonicated for 3 minutes on ice, and the supernatant recovered by centrifugation (10 rpm, 10 min, 4° C. in a Beckmann J2-21 rotor) and loaded onto a TALON metal affinity resin column (Clontech). The column was washed twice with column buffer (50 mM NaH$_2$PO$_4$, 10 mM Tris, 100 mM NaCl [pH8.0] and eluted with 6 ml column buffer containing 50 mM imidazole (fractions I1–I12) followed by 1 ml column buffer containing 100 mM imidazole (fractions 112 and 114). The eluate fractions (0.5 ml each) were analyzed by SDS-PAGE to determine the peak fractions containing CCTδ apical domain (i.e. fractions I4–I14).

Interaction of Chaperonin with Immobilised β-Actin Peptides

A set of seventy-three Pepset™ peptides (Meltek Scientific Ltd) scanning the 375 amino acid residues of mouse β-actin sequence were synthesized on polyethylene solid phase pins in a 96-well format. Each peptide was 15 residues in length; starting from the amino terminal peptide, (#1) $^1$MDDDIAALVVDNGSG$^{15}$ (SEQ ID NO: 25) each subsequent peptide was offset by 5 residues, i.e. (#2) $^6$AALVVD-NGSGMCKAG$^{20}$ (SEQ ID NO: 26), (#3) $^{11}$DNGSGMCK-AGFAGDD$^{25}$ (SEQ ID NO: 27) etc. To detect the interaction of holochaperonin or isolated chaperonin apical domains with the immobilised peptide array, an assay was developed involving monoclonal antibody (MAb) binding followed by ELISA detection.

Non-specific binding to the peptide pins was reduced by incubation with pre-coat buffer (2% BSA, 0.1% Tween 20 in PBS.A pH7.2) for one hour at room temperature. Chaperonin (CCT, GroEL or isolated CCT5 apical domain) was diluted to a concentration of X-Yµg/ml in binding buffer (50 mM HEPES pH 7.2, 90 mM KCl, 0.5 mM MgCl$_2$) and incubated with the peptide pins for 16 hours at 4° C. The pins were washed three times with PBS for a total of 30 minutes, and incubated with the appropriate MAb for 2 hours at room temperature; CCT was detected using MAb 91a (Willison et al Cell, 57, 621–632, 1989), which recognizes the CCTA subunit, GroEL was detected by MAb 4-3F (a kind gift from Dr P Lund, University of Birmingham) and isolated CCTδ apical domain, tagged with a C-terminally located-GALDD (SEQ ID NO: 119) pentapeptide, was detected by MAb 23c (Harrison Lavoie, EMBO J. 12, 2847–2853, 1993) or one isolated CCTδ apical domain, tagged at the C-terminus with a His6 motif, was detected by MAb HIS1 (Sigma). Following washing in PBS, the pins were incubated with a secondary antibody conjugated to alkaline phosphatase (5 µg/ml in PBS, Pierce) for 2 hours at room temperature. The pins were washed in PBS and incubated with p-Nitrophenyl phosphate (Sigma) in a 96-well microtitre plate for 30 minutes in the dark. Absorbance at 410 nm due to the conjugates was detected using an ELISA plate reader.

ATP-Dependent Dissociation of CCT from β-Actin Peptides

The immobilised peptide array was incubated with CCT as described above, and prior to the development step in p-Nitrophenyl phosphate, the peptide pins were incubated at 37° C. for 2 hours in substrate release buffer (50 mM HEPES pH 7.2, 90 mM KCl, 2 mM MgCl$_2$, 1 mM DTT, 1 mM ATP).

Assay to Screen for Interaction of Molecular Chaperones With an Immobilised β-Actin Peptide Array A set of seventy-four Pepset™ peptides (Meltek Scientific) was synthesized on polyethylene solid phase pins in a 96-well format. Each peptide was immobilised at the C-terminus and contained 15 amino acid residues and an acid N-terminus. Peptides 1 to 73 scanned the primary structure of mouse cytoplasmic β-actin (SwissProt:P$_{Q2570}$), and starting from the amino terminal peptide (#1) $^1$MDDDIAALV-VDNGSG$^{15}$ (SEQ ID NO: 25) each subsequent peptide was offset by 5 residues, i.e. (#2) $^6$AALVVDNGSGMCKAG$^{20}$ (SEQ ID NO: 26), (#3) $^{11}$DNGSGMCKAGFAGDD$^{25}$ (SEQ ID NO: 27) etc, Peptide 74 contained the epitope sequence for monoclonal antibody (MAb) 91a, which recognizes CCTA (Willison et al, Cell, 57, 621–632, 1989). An assay to detect the interaction of molecular chaperone proteins with the peptide array involved MAb binding followed by ELISA detection. Non-specific binding to the peptide pins was reduced by incubation with pre-coat buffer (2% BSA, 0.1% Tween 20 in PBS.A pH7.2) for one hour at room temperature. Purified molecular chaperones (6.5 µg/ml) or 6.5 nM CCT; 1.25 UG/ML] or 1.47 nM GroEL; 4 fractions (2 ml total) of purified CCT5 apical domain to a volume of 0.2 ml and the protein concentration was calculated to be 0.6 mg/ml approximately 3.6 µg/ml isolated CCTδ apical domain; or 0.675 µg.ml or 6.75 µM Hsp70) in binding buffer (50 mM HEPES pH 7.2, 90 mM KCl, 0.5 mM MgCl$_2$) were incubated with the peptide array for 16 hours at 4° C. The pins were washed three times with PBS for a total of 30 minutes and incubated with the appropriate MAb (approximately 1.5 µg/ml in PBS) for 2 hours at room temperature; CCT was detected with MAb 91a (Willison et al Cell, 57, 621–632, 1989), GroEL was detected with MAb 4-3F (a kind gift from Dr P Lund, University of Birmingham), Hsp70 was detected with Mab 3A3(Affinity Bioreagents), and isolated CCTδ apical domain tagged at the C-terminus with a-GALDD (SEQ ID NO: 119) pentapeptide was detected with MAb 23c (Willison et al Cell, 57, 621–632, 1989). Following washing in PBS, the pins were incubated with a secondary antibody conjugated to alkaline phosphatase (30 ng/ml in PBS, Pierce) for 2 hours at room temperature. The pins were washed in PBS and incubated with p-Nitrophenyl phosphate (Sigma) in 96-well microtitre plate for 30 minutes in the dark. Absorbance at 410 nm due to the conjugates was detected using a microplate reader (Model MR 710, Dynatech).

ATP-Dependent Dissociation of CCT From β-Actin Peptides

The immobilised peptide array was incubated with CCT as described above and, prior to the development step in p-Nitrophenyl phosphate, the peptide pins were incubated at 37° C. for 2 hours in substrate release buffer (50 mM HEPES pH 7.2, 90 mM KCl, 2 mM MgCl2, 1 mM DTT, 1 mM ATP).

Interaction of Soluble Biotinylated Peptides With CCT

Biotinylated Pepset™ peptides (Meltek Scientific) corresponding to residues 36–50 of mouse β-actin were synthesized on polyethylene solid phase pins, and were chemically cleaved from the solid support to release the peptides. Each peptide contained an amide C-terminus and 19 amino acid residues including a —SGSG (SEQ ID NO: 120) linker to a biotin group at the N-terminus. The set consisted of the wild-type β-actin sequence (biotin-SGSG-$^{36}$GR-PRHQGVMVGMGQK$^{50}$, SEQ ID NO: 18), five mutant peptides containing alanine scanning substitutions of residues GRPRH (SEQ ID NO: 121)
(biotin-SGSG-ARPRHQGVMVGMGQK, SEQ ID NO: 19;
biotin-SGSG-GAPRHQGVMVGMGQK, SEQ ID NO: 20;
biotin-SGSG-GFARHQGVMVGMGQK, SEQ ID NO: 21;
biotin-SGSG-GRPAHQGVMVGMGQK, SEQ ID NO: 22; and
biotin-SGSG-GRPRAQGVMVGMGQK, SEQ ID NO: 23)

and one mutant peptide where all five residues of the GRPRH (SEQ ID NO: 121) core sequence were replaced by AAAAA (SEQ ID NO: 122)(biotin-SGSG-AAAAAQGVMVGMGQK, SEQ ID NO: 24). The peptides were solubilised in 10% acetic acid and analysed by MALDI-MS on a Finnegan Lasermat 2000, and peptide concentration was determined by amino acid analysis. CCT (70 nM) was incubated with peptide (13.3 μm or 1.33 μM) in binding buffer (50 mM HEPES pH 7.2, 90 mM KCl, 0.5 mM MgCl$_2$) for one hour on ice. CCT complex was resolved on 6% native-PAGE gels, electrotransferred to ntirocellulose membrane, incubated with Neutravidin-HRP (Pierce) (2 ug/ml in 2% BSA/PBS) in order to detect the interaction between CCT and biotinylated peptide.

TABLE 2

| mouse beta actin - 15 mer peptides with 5 residue overlap | |
|---|---|
| 1, MDDDIAALVVDNGSG = | 1–15 |
| 2, AALVVDNGSGMCKAG = | 6–20 |
| 3, DNGSGMCKAGFAGDD = | 11–25 |
| 4, MCKAGFAGDDAPRAV = | 16–30 |
| 5, FAGDDAPRAVFPSIV = | 21–35 |
| 6, APRAVFPSIVGRPRH = | 26–40 |
| 7, FPSIVGRPRHQGVMV = | 31–45 |
| 8, GRPRHQGVMVGMGQK = | 36–50 |
| 9, QGVMVGMGQKDSYVG = | 41–55 |
| 10, GMGQKDSYVGDEAQS = | 46–60 |
| 11, DSYVGDEAQSKRGIL = | 51–65 |
| 12, DEAQSKRGILTLKYP = | 56–70 |
| 13, KRGILTLKYPIEHGI = | 61–75 |
| 14, TLKYPIEHGIVTNWD = | 66–80 |
| 15, IEHGIVTNWDDMEKI = | 71–85 |
| 16, VTNWDDMEKIWHHTF = | 76–90 |
| 17, DMEKIWHHTFYNELR = | 81–95 |
| 18, WHHTFYNELRVAPEE = | 86–100 |
| 19, YNELRVAPEEHPVLL = | 91–105 |
| 20, VAPEEHPVLLTEAPL = | 96–110 |
| 21, HPVLLTEAPLNPKAN = | 101–115 |
| 22, TEAPLNPKANREKMT = | 106–120 |
| 23, NPKANREKMTQIMFE = | 111–125 |
| 24, REKMTQIMFETFNTP = | 116–130 |
| 25, QIMFETFNTPAMYVA = | 121–135 |
| 26, TFNTPAMYVAIQAVL = | 126–140 |
| 27, AMYVAIQAVLSLYAS = | 131–145 |
| 28, IQAVLSLYASGRTTG = | 136–150 |
| 29, SLYASGRTTGIVMDS = | 141–155 |
| 30, GRTTGIVMDSGDGVT = | 146–160 |
| 31, IVMDSGDGVTHTVPI = | 151–165 |
| 32, GDGVTHTVPIYEGYA = | 156–170 |
| 33, HTVPIYEGYALPHAI = | 161–175 |
| 34, YEGYALPHAILRLDL = | 166–180 |
| 35, LPHAILRLDLAGRDL = | 171–185 |
| 36, LRLDLAGRDLTDYLM = | 176–190 |
| 37, AGRDLTDYLMKILTE = | 181–195 |
| 38, TDYLMKILTERGYSF = | 186–200 |
| 39, KILTERGYSFTTTAE = | 191–205 |
| 40, RGYSFTTTAEREIVR = | 196–210 |
| 41, TTTAEREIVRDIKEK = | 201–215 |
| 42, REIVRDIKEKLCYVA = | 206–220 |

TABLE 2-continued

| mouse beta actin - 15 mer peptides with 5 residue overlap | |
|---|---|
| 43, DIKEKLCYVALDFEQ = | 211–225 |
| 44, LCYVALDFEQEMATA = | 216–230 |
| 45, LDFEQEMATAASSSS = | 221–235 |
| 46, EMATAASSSSLEKSY = | 226–240 |
| 47, ASSSSLEKSYELPDG = | 231–245 |
| 48, LEKSYELPDGQVITI = | 236–250 |
| 49, ELPDGQVITIGNERF = | 241–255 |
| 50, QVITIGNERFRCPEA = | 246–260 |
| 51, GNERFRCPEALFQPS = | 251–265 |
| 52, RCPEALFQPSFLGME = | 256–270 |
| 53, LFQPSFLGMESCGIH = | 261–275 |
| 54, FLGMESCGIHETTFN = | 266–280 |
| 55, SCGIHETTFNSIMKC = | 271–285 |
| 56, ETTFNSIMKCDVDIR = | 276–290 |
| 57, SIMKCDVDIRKDLYA = | 281–295 |
| 58, DVDIRKDLYANTVLS = | 286–300 |
| 59, KDLYANTVLSGGTTM = | 291–305 |
| 60, NTVLSGGTTMYPGIA = | 296–310 |
| 61, GGTTMYPGIADRMQK = | 301–315 |
| 62, YPGIADRMQKEITAL = | 306–320 |
| 63, DRMQKEITALAPSTM = | 311–325 |
| 64, EITALAPSTMKIKII = | 316–330 |
| 65, APSTMKIKIIAPPER = | 321–335 |
| 66, KIKIIAPPERKYSVW = | 326–340 |
| 67, APPERKYSVWIGGSI = | 331–345 |
| 68, KYSVWIGGSILASLS = | 336–350 |
| 69, IGGSILASLSTFQQM = | 341–355 |
| 70, LASLSTFQQMWISKQ = | 346–360 |
| 71, TFQQMWISKQEYDES = | 351–365 |
| 72, WISKQEYDESGPSIV = | 356–370 |
| 73, EYDESGPSIVHRKCF = | 361–375 |
| 74, GGGGGGPSIVHRKCF = | 366–375 |
| 75, GGGGGGGGGGHRKCF = | 371–375 |
| Other peptides to include: | |

76, KYSVWIGGSILASLS
alpha helix in subdomain 1 of rabbit alpha actin-contains two hydrophobic residues accessible to solvent
(residues S338–S348)
77, PRHQGVMVGMGQKDS
loop in subdomain 2 of rabbit alpha actin-major interaction site with DNase I
(residues P38–S52)
78, IVLDSGDGVTHNVPI
beta stands in subdomain 3 of rabbit alpha actin
(residues G150–Y166)
79, LVCDNGSGLVKAGFA
analogous beta strand motif in subdomain 1 of rabbit alpha actin
(residues L8–F21)
80, LFQPSFIGMESAGIH
loop in subdomain 4 of rabbit alpha actin-involved in contact across helix axis in F-actin
(residues F262–L274)
81, TTAEREIVRDIKEKL
Alpha helix in subdomain 4 of rabbit alpha actin-minor interaction site with DNase I
(residues T203–L216)
82, YVGDEAQSKRGILTL
beta alpha beta unit in subdomain 2 of rabbit alpha actin-minor interaction site with DNase I/ hexokinase-like unit
(residues K61–L65)
83, VMSGGTTMYPGIADR
loop in subdomain 3 of rabbit alpha actin-forms pocket for adenine base of nucleotide
(residues S300–I309)
84, KIKIIAPPERKYSVW
beta strand and loop in subdomain 3 of rabbit alpha actin-forms pocket for adenine base of nucleotide
(residues K328–S338)
85, GFAGDDAPRAVFPSI
loop in subdomain 1 of rabbit alpha actin-central contact region of myosin on 'flat' side of actin
(residues F21–P32)

TABLE 2-continued mouse beta actin - 15 mer peptides with 5 residue overlap

86, YNELRVAPEEHPTLL
loop in subdomain 1 of rabbit alpha actin-contact region
of myosin on 'flat' side of actin
(residues N92–T103)

87, TFQQMWITKQEYDEA
alpha helices in subdomain 1 of rabbit alpha actin-bind
myosin chains
(residues S348–A365)

88, DEDETTALVCDNGSG
N-terminal 15 residues of rabbit alpha actin-important in
binding myosin
(residues D1–G15)

89, EYDEAGPSIVHRKCF
C-terminal 15 residues of rabbit alpha actin
(residues E361–F375)

TABLE 2-continued mouse beta actin - 15 mer peptides with 5 residue overlap

90, SKQEYDESGPSIVHR
truncated C-terminus of mouse beta actin
(residues S358–R372)

91, ILTERGYSFVTTAER
loop in subdomain 4 of rabbit alpha actin-analagous to
DNase I-binding loop in subdomain 2
(residues T194–T203)

92, ALDFENEMATAASSS
alpha helix flanked by loops in subdomain 4 of rabbit
alpha actin
(residues F223–A230)

93, WDDMEKIWHHTFYNE
alpha helix in subdomain 1 of rabbit alpha actin
(residues W79–N92)

94, +ve control for 91a = STDLVAKLRAFHNEA

What is claimed is:

1. A method for identifying a binding member capable of occupying a substrate binding site on the CCT complex or part thereof, wherein the binding member inhibits the binding of the CCT substrate to the CCT complex or part thereof.

2. A method according to claim 1 wherein the binding member is an antibody.

3. A method according to claim 1 wherein the binding member is a peptide.

4. A method according to claim 3 wherein the binding member is greater than 5 amino acids in length.

5. A method according to claim 4 wherein the binding member is from 5 to 40 amino acids in length.

6. A method according to claim 3 wherein the binding member is derived from a CCT substrate.

7. A method according to claim 6 wherein the substrate from which the binding member is derived is selected from the group consisting of actin, tubulin or cyclin.

8. A method according to claim 7 wherein the substrate from which the binding member is derived is actin.

9. A method according to claim 3 wherein the binding member comprises a sequence selected from the group of SEQ ID NOS: 1–15.

10. A method according to claim 9 wherein the binding member comprises the amino acid sequence GRPRH (SEQ ID NO: 121).

11. A method of identifying a binding member capable of occupying a substrate binding site on a CCT apical domain; comprising the steps of
    contacting a candidate binding member with said CCT apical domain; and
    determining binding between said candidate binding member and the CCT apical domain
wherein the binding member inhibits the binding of the CCT substrate to the CCT apical domain.

12. A method according to claim 11 wherein the binding member is a peptide.

13. A method according to claim 12 wherein the candidate binding member is a peptide having an amino acid sequence corresponding to the amino acid sequence of a CCT substrate.

14. A method according to claim 13 wherein the CCT substrate is actin.

15. A method according to claim 14 wherein the CCT substrate is tubulin.

16. A method according to claim 12 wherein the peptide comprises a sequence selected from the group of sequences shown in SEQ ID NOS 1–15.

17. A method according to claim 11 further comprising the step of immobilizing the candidate binding member on a solid phase prior to contacting with the CCT apical domain.

18. A method according to claim 11 wherein binding between the candidate binding member and the CCT apical domain is determined by a competitive assay.

* * * * *

```
                               SEQUENCE LISTING

<160> NUMBER OF SEQ ID NOS: 123

<210> SEQ ID NO 1
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 1

Ala Pro Arg Ala Val Phe Pro Ser Ile Val Gly Arg Pro Arg His
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 2

Phe Pro Ser Ile Val Gly Arg Pro Arg His Gln Gly Val Met Val
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 3

Gly Arg Pro Arg His Gln Gly Val Met Val Gly Met Gly Gln Lys
1               5                   10                  15

<210> SEQ ID NO 4
<211> LENGTH: 15
<212> TYPE: PRT
```

```
<213> ORGANISM: Artificial Sequence
<220> FEATURE:
<223> OTHER INFORMATION: Synthetic Sequence

<400> SEQUENCE: 4

Gly Gly Thr Thr Met Tyr Pro Gly Ile Ala Asp Arg Met Gln Lys
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 5

Pro Arg His Gln Gly Val Met Val Gly Met Gly Lys Asp Ser
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 6

Thr Phe Asn Thr Pro Ala Met Tyr Val Ala Ile Gln Ala Val Leu
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic sequence

<400> SEQUENCE: 7

Leu Pro His Ala Ile Leu Arg Leu Asp Leu Ala Gly Arg Asp Leu
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 8

Leu Ala Ser Leu Ser Thr Phe Gln Gln Met Trp Ile Ser Lys Gln
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 9

Asp Glu Ala Gln Ser Lys Arg Gly Ile Leu Thr Leu Lys Tyr Pro
 1               5                  10                  15

<210> SEQ ID NO 10
<211> LENGTH: 15
<212> TYPE: PRT
<213> ORGANISM: Artificial Sequence
```

```
<220> FEATURE:
<223> OTHER INFORMATION: Synthetic Sequence

<400> SEQUENCE: 10

Ile Gln Ala Val Leu Ser Leu Tyr Ala Ser Gly Arg Thr Thr Gly
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 11

Lys Ile Leu Thr Glu Arg Gly Tyr Ser Phe Thr Thr Thr Ala Glu
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 12

Arg Gly Tyr Ser Phe Thr Thr Thr Ala Glu Arg Glu Ile Val Arg
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 13

Ala Ser Ser Ser Ser Leu Glu Lys Ser Tyr Glu Leu Pro Asp Gly
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 14

Ala Pro Ser Thr Met Lys Ile Lys Ile Ile Ala Pro Pro Glu Arg
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 15

Ala Pro Pro Glu Arg Lys Tyr Ser Val Trp Ile Gly Gly Ser Ile
 1               5                  10                  15

<210> SEQ ID NO 16
<211> LENGTH: 9
<212> TYPE: PRT
<213> ORGANISM: Artificial Sequence
<220> FEATURE:
```

<223> OTHER INFORMATION: Synthetic Sequence

<400> SEQUENCE: 16

Ala Val His Ser Gly Ala Leu Asp Asp
 1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 17

Ala Val His Ser Gly Ala Leu Asn Asp
 1               5

<210> SEQ ID NO 18
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 18

Ser Gly Ser Gly Gly Arg Pro Arg His Gln Gly Val Met Val Gly Met
 1               5                  10                  15

Gly Gln Lys

<210> SEQ ID NO 19
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 19

Ser Gly Ser Gly Ala Arg Pro Arg His Gln Gly Val Met Val Gly Met
 1               5                  10                  15

Gly Gln Lys

<210> SEQ ID NO 20
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 20

Ser Gly Ser Gly Gly Ala Pro Arg His Gln Gly Val Met Val Gly Met
 1               5                  10                  15

Gly Gln Lys

<210> SEQ ID NO 21
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 21

Ser Gly Ser Gly Gly Arg Ala Arg His Gln Gly Val Met Val Gly Met
 1               5                  10                  15

Gly Gln Lys

-continued

```
<210> SEQ ID NO 22
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 22

Ser Gly Ser Gly Gly Arg Pro Ala His Gln Gly Val Met Val Gly Met
 1               5                  10                  15

Gly Gln Lys

<210> SEQ ID NO 23
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 23

Ser Gly Ser Gly Gly Arg Pro Arg Ala Gln Gly Val Met Val Gly Met
 1               5                  10                  15

Gly Gln Lys

<210> SEQ ID NO 24
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 24

Ser Gly Ser Gly Ala Ala Ala Ala Gln Gly Val Met Val Gly Met
 1               5                  10                  15

Gly Gln Lys

<210> SEQ ID NO 25
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 25

Met Asp Asp Asp Ile Ala Ala Leu Val Val Asp Asn Gly Ser Gly
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 26

Ala Ala Leu Val Val Asp Asn Gly Ser Gly Met Cys Lys Ala Gly
 1               5                  10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Sequence
```

```
<400> SEQUENCE: 27

Asp Asn Gly Ser Gly Met Cys Lys Ala Gly Phe Ala Gly Asp Asp
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 28

Met Cys Lys Ala Gly Phe Ala Gly Asp Asp Ala Pro Arg Ala Val
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 29

Phe Ala Gly Asp Asp Ala Pro Arg Ala Val Phe Pro Ser Ile Val
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 30

Ala Pro Arg Ala Val Phe Pro Ser Ile Val Gly Arg Pro Arg His
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 31

Phe Pro Ser Ile Val Gly Arg Pro Arg His Gln Gly Val Met Val
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 32

Gly Arg Pro Arg His Gln Gly Val Met Val Gly Met Gly Gln Lys
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic Sequence
```

-continued

<400> SEQUENCE: 33

Gln Gly Val Met Val Gly Met Gly Gln Lys Asp Ser Tyr Val Gly
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 34

Gly Met Gly Gln Lys Asp Ser Tyr Val Gly Asp Glu Ala Gln Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 35

Asp Ser Tyr Val Gly Asp Glu Ala Gln Ser Lys Arg Gly Ile Leu
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 36

Asp Glu Ala Gln Ser Lys Arg Gly Ile Leu Thr Leu Lys Tyr Pro
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 37

Lys Arg Gly Ile Leu Thr Leu Lys Tyr Pro Ile Glu His Gly Ile
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 38

Thr Leu Lys Tyr Pro Ile Glu His Gly Ile Val Thr Asn Trp Asp
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 39

```
Ile Glu His Gly Ile Val Thr Asn Trp Asp Asp Met Glu Lys Ile
 1               5                  10                  15
```

<210> SEQ ID NO 40
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 40

```
Val Thr Asn Trp Asp Asp Met Glu Lys Ile Trp His His Thr Phe
 1               5                  10                  15
```

<210> SEQ ID NO 41
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 41

```
Asp Met Glu Lys Ile Trp His His Thr Phe Tyr Asn Glu Leu Arg
 1               5                  10                  15
```

<210> SEQ ID NO 42
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 42

```
Trp His His Thr Phe Tyr Asn Glu Leu Arg Val Ala Pro Glu Glu
 1               5                  10                  15
```

<210> SEQ ID NO 43
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 43

```
Tyr Asn Glu Leu Arg Val Ala Pro Glu Glu His Pro Val Leu Leu
 1               5                  10                  15
```

<210> SEQ ID NO 44
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 44

```
Val Ala Pro Glu Glu His Pro Val Leu Leu Thr Glu Ala Pro Leu
 1               5                  10                  15
```

<210> SEQ ID NO 45
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 45

```
His Pro Val Leu Leu Thr Glu Ala Pro Leu Asn Pro Lys Ala Asn
 1               5                  10                  15
```

<210> SEQ ID NO 46
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 46

```
Thr Glu Ala Pro Leu Asn Pro Lys Ala Asn Arg Glu Lys Met Thr
 1               5                  10                  15
```

<210> SEQ ID NO 47
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 47

```
Asn Pro Lys Ala Asn Arg Glu Lys Met Thr Gln Ile Met Phe Glu
 1               5                  10                  15
```

<210> SEQ ID NO 48
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 48

```
Arg Glu Lys Met Thr Gln Ile Met Phe Glu Thr Phe Asn Thr Pro
 1               5                  10                  15
```

<210> SEQ ID NO 49
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 49

```
Gln Ile Met Phe Glu Thr Phe Asn Thr Pro Ala Met Tyr Val Ala
 1               5                  10                  15
```

<210> SEQ ID NO 50
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 50

```
Thr Phe Asn Thr Pro Ala Met Tyr Val Ala Ile Gln Ala Val Leu
 1               5                  10                  15
```

<210> SEQ ID NO 51
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 51

Ala Met Tyr Val Ala Ile Gln Ala Val Leu Ser Leu Tyr Ala Ser

```
                1               5              10              15

<210> SEQ ID NO 52
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 52

Ile Gln Ala Val Leu Ser Leu Tyr Ala Ser Gly Arg Thr Thr Gly
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 53

Ser Leu Tyr Ala Ser Gly Arg Thr Thr Gly Ile Val Met Asp Ser
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 54

Gly Arg Thr Thr Gly Ile Val Met Asp Ser Gly Asp Gly Val Thr
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 55

Ile Val Met Asp Ser Gly Asp Gly Val Thr His Thr Val Pro Ile
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 56

Gly Asp Gly Val Thr His Thr Val Pro Ile Tyr Glu Gly Tyr Ala
 1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 57

His Thr Val Pro Ile Tyr Glu Gly Tyr Ala Leu Pro His Ala Ile
 1               5                  10                  15
```

-continued

<210> SEQ ID NO 58
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 58

Tyr Glu Gly Tyr Ala Leu Pro His Ala Ile Leu Arg Leu Asp Leu
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 59

Leu Pro His Ala Ile Leu Arg Leu Asp Leu Ala Gly Arg Asp Leu
 1               5                  10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 60

Leu Arg Leu Asp Leu Ala Gly Arg Asp Leu Thr Asp Tyr Leu Met
 1               5                  10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 61

Ala Gly Arg Asp Leu Thr Asp Tyr Leu Met Lys Ile Leu Thr Glu
 1               5                  10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 62

Thr Asp Tyr Leu Met Lys Ile Leu Thr Glu Arg Gly Tyr Ser Phe
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 63

Lys Ile Leu Thr Glu Arg Gly Tyr Ser Phe Thr Thr Thr Ala Glu
 1               5                  10                  15

```
<210> SEQ ID NO 64
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 64

Arg Gly Tyr Ser Phe Thr Thr Thr Ala Glu Arg Glu Ile Val Arg
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 65

Thr Thr Thr Ala Glu Arg Glu Ile Val Arg Asp Ile Lys Glu Lys
 1               5                  10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 66

Arg Glu Ile Val Arg Asp Ile Lys Glu Lys Leu Cys Tyr Val Ala
 1               5                  10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 67

Asp Ile Lys Glu Lys Leu Cys Tyr Val Ala Leu Asp Phe Glu Gln
 1               5                  10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 68

Leu Cys Tyr Val Ala Leu Asp Phe Glu Gln Glu Met Ala Thr Ala
 1               5                  10                  15

<210> SEQ ID NO 69
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 69

Leu Asp Phe Glu Gln Glu Met Ala Thr Ala Ala Ser Ser Ser Ser
 1               5                  10                  15
```

```
<210> SEQ ID NO 70
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 70

Glu Met Ala Thr Ala Ala Ser Ser Ser Leu Glu Lys Ser Tyr
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 71

Ala Ser Ser Ser Ser Leu Glu Lys Ser Tyr Glu Leu Pro Asp Gly
 1               5                  10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 72

Leu Glu Lys Ser Tyr Glu Leu Pro Asp Gly Gln Val Ile Thr Ile
 1               5                  10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 73

Glu Leu Pro Asp Gly Gln Val Ile Thr Ile Gly Asn Glu Arg Phe
 1               5                  10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 74

Gln Val Ile Thr Ile Gly Asn Glu Arg Phe Arg Cys Pro Glu Ala
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 75

Gly Asn Glu Arg Phe Arg Cys Pro Glu Ala Leu Phe Gln Pro Ser
 1               5                  10                  15

<210> SEQ ID NO 76
```

```
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 76

Arg Cys Pro Glu Ala Leu Phe Gln Pro Ser Phe Leu Gly Met Glu
 1               5                  10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 77

Leu Phe Gln Pro Ser Phe Leu Gly Met Glu Ser Cys Gly Ile His
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 78

Phe Leu Gly Met Glu Ser Cys Gly Ile His Glu Thr Thr Phe Asn
 1               5                  10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 79

Ser Cys Gly Ile His Glu Thr Thr Phe Asn Ser Ile Met Lys Cys
 1               5                  10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 80

Glu Thr Thr Phe Asn Ser Ile Met Lys Cys Asp Val Asp Ile Arg
 1               5                  10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 81

Ser Ile Met Lys Cys Asp Val Asp Ile Arg Lys Asp Leu Tyr Ala
 1               5                  10                  15

<210> SEQ ID NO 82
<211> LENGTH: 15
```

-continued

```
<212> TYPE: PRT
<213> ORGANISM: Artificial Sequence
<220> FEATURE:
<223> OTHER INFORMATION: Synthetic Sequence

<400> SEQUENCE: 82

Asp Val Asp Ile Arg Lys Asp Leu Tyr Ala Asn Thr Val Leu Ser
  1               5                  10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 83

Lys Asp Leu Tyr Ala Asn Thr Val Leu Ser Gly Gly Thr Thr Met
  1               5                  10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 84

Asn Thr Val Leu Ser Gly Gly Thr Thr Met Tyr Pro Gly Ile Ala
  1               5                  10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 85

Gly Gly Thr Thr Met Tyr Pro Gly Ile Ala Asp Arg Met Gln Lys
  1               5                  10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 86

Tyr Pro Gly Ile Ala Asp Arg Met Gln Lys Glu Ile Thr Ala Leu
  1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 87

Asp Arg Met Gln Lys Glu Ile Thr Ala Leu Ala Pro Ser Thr Met
  1               5                  10                  15

<210> SEQ ID NO 88
<211> LENGTH: 15
<212> TYPE: PRT
```

```
<213> ORGANISM: Artificial Sequence
<220> FEATURE:
<223> OTHER INFORMATION: Synthetic Sequence

<400> SEQUENCE: 88

Glu Ile Thr Ala Leu Ala Pro Ser Thr Met Lys Ile Lys Ile Ile
 1               5                  10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 89

Ala Pro Ser Thr Met Lys Ile Lys Ile Ile Ala Pro Pro Glu Arg
 1               5                  10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 90

Lys Ile Lys Ile Ile Ala Pro Pro Glu Arg Lys Tyr Ser Val Trp
 1               5                  10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 91

Ala Pro Pro Glu Arg Lys Tyr Ser Val Trp Ile Gly Gly Ser Ile
 1               5                  10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 92

Lys Tyr Ser Val Trp Ile Gly Gly Ser Ile Leu Ala Ser Leu Ser
 1               5                  10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 93

Ile Gly Gly Ser Ile Leu Ala Ser Leu Ser Thr Phe Gln Gln Met
 1               5                  10                  15

<210> SEQ ID NO 94
<211> LENGTH: 15
<212> TYPE: PRT
<213> ORGANISM: Artificial Sequence
```

-continued

```
<220> FEATURE:
<223> OTHER INFORMATION: Synthetic Sequence

<400> SEQUENCE: 94

Leu Ala Ser Leu Ser Thr Phe Gln Gln Met Trp Ile Ser Lys Gln
 1               5                  10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 95

Thr Phe Gln Gln Met Trp Ile Ser Lys Gln Glu Tyr Asp Glu Ser
 1               5                  10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 96

Trp Ile Ser Lys Gln Glu Tyr Asp Glu Ser Gly Pro Ser Ile Val
 1               5                  10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 97

Glu Tyr Asp Glu Ser Gly Pro Ser Ile Val His Arg Lys Cys Phe
 1               5                  10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 98

Gly Gly Gly Gly Gly Gly Pro Ser Ile Val His Arg Lys Cys Phe
 1               5                  10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 99

Gly Gly Gly Gly Gly Gly Gly Gly Gly Gly His Arg Lys Cys Phe
 1               5                  10                  15

<210> SEQ ID NO 100
<211> LENGTH: 15
<212> TYPE: PRT
<213> ORGANISM: Artificial Sequence
<220> FEATURE:
```

```
<223> OTHER INFORMATION: Synthetic Sequence

<400> SEQUENCE: 100

Lys Tyr Ser Val Trp Ile Gly Gly Ser Ile Leu Ala Ser Leu Ser
 1               5                  10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 101

Pro Arg His Gln Gly Val Met Val Gly Met Gly Gln Lys Asp Ser
 1               5                  10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 102

Ile Val Leu Asp Ser Gly Asp Gly Val Thr His Asn Val Pro Ile
 1               5                  10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 103

Leu Val Cys Asp Asn Gly Ser Gly Leu Val Lys Ala Gly Phe Ala
 1               5                  10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 104

Leu Phe Gln Pro Ser Phe Ile Gly Met Glu Ser Ala Gly Ile His
 1               5                  10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 105

Thr Thr Ala Glu Arg Glu Ile Val Arg Asp Ile Lys Glu Lys Leu
 1               5                  10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic Sequence
```

-continued

<400> SEQUENCE: 106

Tyr Val Gly Asp Glu Ala Gln Ser Lys Arg Gly Ile Leu Thr Leu
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 107

Val Met Ser Gly Gly Thr Thr Met Tyr Pro Gly Ile Ala Asp Arg
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 108

Lys Ile Lys Ile Ile Ala Pro Pro Glu Arg Lys Tyr Ser Val Trp
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 109

Gly Phe Ala Gly Asp Asp Ala Pro Arg Ala Val Phe Pro Ser Ile
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 110

Tyr Asn Glu Leu Arg Val Ala Pro Glu Glu His Pro Thr Leu Leu
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 111

Thr Phe Gln Gln Met Trp Ile Thr Lys Gln Glu Tyr Asp Glu Ala
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic Sequence

```
<400> SEQUENCE: 112

Asp Glu Asp Glu Thr Thr Ala Leu Val Cys Asp Asn Gly Ser Gly
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 113

Glu Tyr Asp Glu Ala Gly Pro Ser Ile Val His Arg Lys Cys Phe
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 114

Ser Lys Gln Glu Tyr Asp Glu Ser Gly Pro Ser Ile Val His Arg
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 115

Ile Leu Thr Glu Arg Gly Tyr Ser Phe Val Thr Thr Ala Glu Arg
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 116

Ala Leu Asp Phe Glu Asn Glu Met Ala Thr Ala Ala Ser Ser Ser
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 117

Trp Asp Asp Met Glu Lys Ile Trp His His Thr Phe Tyr Asn Glu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 118
```

```
Ser Thr Asp Leu Val Ala Lys Leu Arg Ala Phe His Asn Glu Ala
1               5                   10                  15

<210> SEQ ID NO 119
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 119

Gly Ala Leu Asp Asp
1               5

<210> SEQ ID NO 120
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 120

Ser Gly Ser Gly
1

<210> SEQ ID NO 121
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 121

Gly Arg Pro Arg His
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 122

Ala Ala Ala Ala Ala
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 123

Gly Ala Pro Ala His
1               5
```